(12) United States Patent
McNair

(10) Patent No.: US 11,646,098 B1
(45) Date of Patent: May 9, 2023

(54) FORECASTING MACROPHAGE ACTIVATION SYNDROMES

(71) Applicant: CERNER INNOVATION, INC., Kansas City, KS (US)

(72) Inventor: Douglas S. McNair, Leawood, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 1336 days.

(21) Appl. No.: 15/717,777

(22) Filed: Sep. 27, 2017

Related U.S. Application Data

(60) Provisional application No. 62/401,843, filed on Sep. 29, 2016.

(51) Int. Cl.

| | |
|---|---|
| *G16B 5/00* | (2019.01) |
| *G16H 10/60* | (2018.01) |
| *G06Q 10/10* | (2012.01) |
| *G16H 50/50* | (2018.01) |
| *G06Q 10/1093* | (2023.01) |

(52) U.S. Cl.
CPC ............... *G16B 5/00* (2019.02); *G16H 10/60* (2018.01); *G06Q 10/1095* (2013.01); *G16H 50/50* (2018.01)

(58) Field of Classification Search
None
See application file for complete search history.

(56) References Cited

PUBLICATIONS

Lavrac (Artificial Intelligence in Medicine (1999) vol. 16:3-23).*
Lehmberg et al. (British Journal of Haematology (2010) vol. 160:275-287).*
Janka et al. (Blood Reviews (2014) vol. 28:135-142).*

\* cited by examiner

*Primary Examiner* — Lori A. Clow
(74) *Attorney, Agent, or Firm* — Kilpatrick Townsend & Stockton LLP

(57) ABSTRACT

Technologies are disclosed for determining or predicting the occurrence of a macrophage activation syndrome, such as hemophagocytic lymphohistiocytosis (HLH). A detection of the emergence of and/or a reliable estimation of the likelihood of future significant macrophage activation syndromes, such as HLH, may be determined or predicted from a time series of laboratory and physiologic values to be measured in a patient. Root mean square of successive deviations (RMSSD) is utilized as a surrogate non-parametric measure of the high-frequency power spectral density (PSD) to identify strong statistical associations with the presence and/or near-term future emergence of macrophage activation syndromes. Utilizing these input variables, a model having satisfactory predictive accuracy is constructed using linear discriminant analysis (LDA), gradient boosting, random forest (RF), neural network, logistic regression, or the like, and may be used for the prediction.

20 Claims, 15 Drawing Sheets

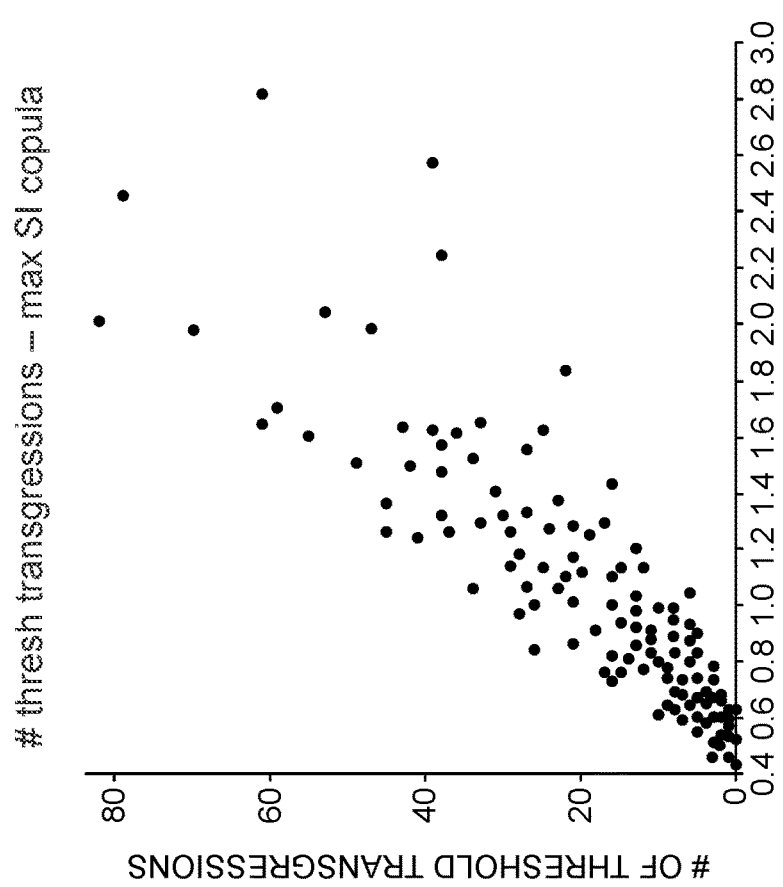
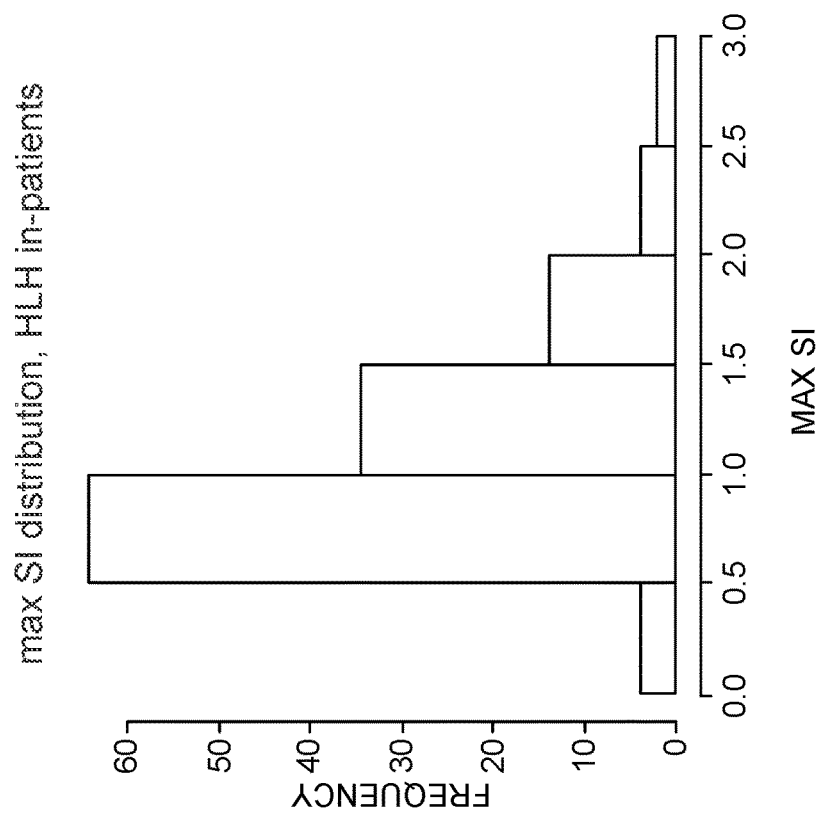
FIG. 5A.
FIG. 5B.

```
##########################################################################

#  HLH copula regression

#################################################################### library(lattice)
library(flexmix)
library(betareg)

library(gcmr)

# load data - y is zero-inflated Poisson count var; x is Gamma or log-normal distributed continuous var
#        - shock index (HR/SBP) 0.30 to 3.80
hlh_si_transgr <- read.csv(file="c:/0_cerdsm/IP/oncology_HLH/hlh3.csv", header=TRUE,
            colClasses=c("numeric","integer"))
x <- hlh_si_transgr[,1]      # maxSI
y <- hlh_si_transgr[,2]      # transgr fit Gaussian copula regression model with negative binomial marginals
mod1 <- gcmr(y ~ x, data=hlh_si_transgr, marginal=negbin.marg, cormat=ind.cormat())

# show results of copula regression fit
summary(mod1)
# Coefficients marginal model:
#          Estimate Std. Error z value Pr(>|z|)
# (Intercept) 0.73372   0.14986   4.896 9.79e-07 ***
# x           1.83678   0.12685  14.480  < 2e-16 ***
# dispersion  0.23471   0.04224   5.557 2.75e-08 ***

log likelihood = 427.18,  AIC = 860.36 generate QQ plot of copula regression fit
plot(mod1, 3, col="gray", lwd=2, cex=1.4)

# generate observed-vs-predicted  plot of copula regression fit
plot(mod1, 4, col="gray", lwd=2, cex=1.4)

# fit Gaussian copula regression model with binomial marginals
mod2 <- gcmr(y ~ x, data=hlh_si_transgr, marginal=binomial.marg, cormat=ind.cormat())

# show results of copula regression fit
summary(mod2)
```

FIG. 6A.

FORECASTING MACROPHAGE ACTIVATION SYNDROMES

CROSS-REFERENCE TO RELATED APPLICATION

This application claims priority to U.S. Provisional Patent Application No. 62/401,843, filed Sep. 29, 2016, entitled "Forecasting Macrophage Activation Syndromes," the entire contents of which are hereby incorporated by reference.

BACKGROUND

Hemophagocytic lymphohistiocytosis (HLH) is a life-threatening syndrome of immune dysregulation and is classified as primary or secondary according to the underlying etiology. Reactive hemophagocytic syndrome is triggered by various infections, hematologic malignancies, and systemic autoimmune diseases (JRA, IM) and is contrasted with familial HLH. The latter condition is associated with mutations in the perforin gene related to T-cell cytotoxicity; both conditions are associated with hypersecretion of pro-inflammatory and Th1 cytokines, including IFN-gamma, IL-1, IL-6, IL-18, and TNF-alpha. In humans, mutations in seven genes encoding proteins involved in cytolytic effector functions have so far been identified that predispose to HLH. However, although most affected patients develop HLH eventually, disease onset and severity are highly variable. Due to the genetic heterogeneity and variable time and nature of disease triggers, the immunological basis of these variations in HLH progression is incompletely understood. Acquired or 'reactive' HLH is related to hematologic malignancy in 72%, infectious disease in 15%, autoimmune disease in 12%, and is multi-factorial in approximately 11% of patients.

Organ dysfunction besides hematologic dysfunction is eventually present in all patients. In many, multi-organ system dysfunction (MOD) eventuates. Hepatic and/or respiratory failure requiring mechanical ventilation are very common (>80%), and in many cases cardiovascular failure and shock supervene (70%). Many manifest neurologic dysfunction including convulsion and coma, and renal failure is present as well, commonly following hemodynamic decompensation or shock. The condition has mortality rates between 18% and 60%. Most deaths occur between 6 and 26 weeks following the onset of the HLH syndrome. Thus, there is typically considerable time during which to establish the diagnosis and undertake immunomodulatory and other treatments. While there have been attempts to provide a technological solution, technology has largely failed to provide a reliable and accurate solution.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Embodiments described in this disclosure are directed towards systems and methods for determining or predicting the occurrence of a macrophage activation syndrome, such as hemophagocytic lymphohistiocytosis (HLH). For example, in an embodiment a detection of the emergence of and/or a reliable estimation of the likelihood of future significant macrophage activation syndromes, such as HLH, may be determined or predicted from a time series of laboratory and physiologic values to be measured in a patient. Further, in some embodiments, the time horizon of the future time interval predicted may range from 72 hours to approximately 30 days, depending on the frequency of laboratory measurements. In particular, embodiments utilize spectrum-analytic and information-theoretic methods that do not require that the measurements be acquired on an especially frequent or regular or periodic basis. Rather, embodiments take advantage of these short- and longer-range patterns in "regularly irregular" phenomena from inconsistencies in times of measuring laboratory and physiologic parameters to produce robust forecasts of near-term risk of hypoglycemia and hyperglycemia.

In one aspect, root mean square of successive deviations (RMSSD) is utilized as a surrogate non-parametric measure of the high-frequency power spectral density (PSD) to identify strong statistical associations with the presence and/or near-term future emergence of macrophage activation syndromes. Utilizing these input variables, a models having satisfactory predictive accuracy may be constructed using linear discriminant analysis (LDA), gradient boosting, random forest (RF), neural network, logistic regression, and/or other, similar classification or regression models. In this way, embodiments of the disclosure are robust against intermittent gaps or failures on the part of the patient or caregiver to perform usual measurements, against delays in uploading or sync'ing newly acquired values with historical time series measured in the patient, and against non-stationarity in the time series such as may arise during periods when the patient's health deviates from predominant patterns, such as when the patient has an acute infection.

BRIEF DESCRIPTION OF THE DRAWINGS

The present invention is described in detail below with reference to the attached drawing figures, wherein:

FIGS. 5A depicts max shock index (SI) distribution in HLH patient, in accordance with an embodiment of this disclosure;

FIGS. 5B depicts the number of threshold transgressions as a function of the max SI index, in accordance with an embodiment of this disclosure;

FIG. 6A illustratively provide an example embodiment of a computer program routine for performing the HLH copula regression utilized to determining or predicting the occurrence of a macrophage activation syndrome.

DETAILED DESCRIPTION

Figure 1A:
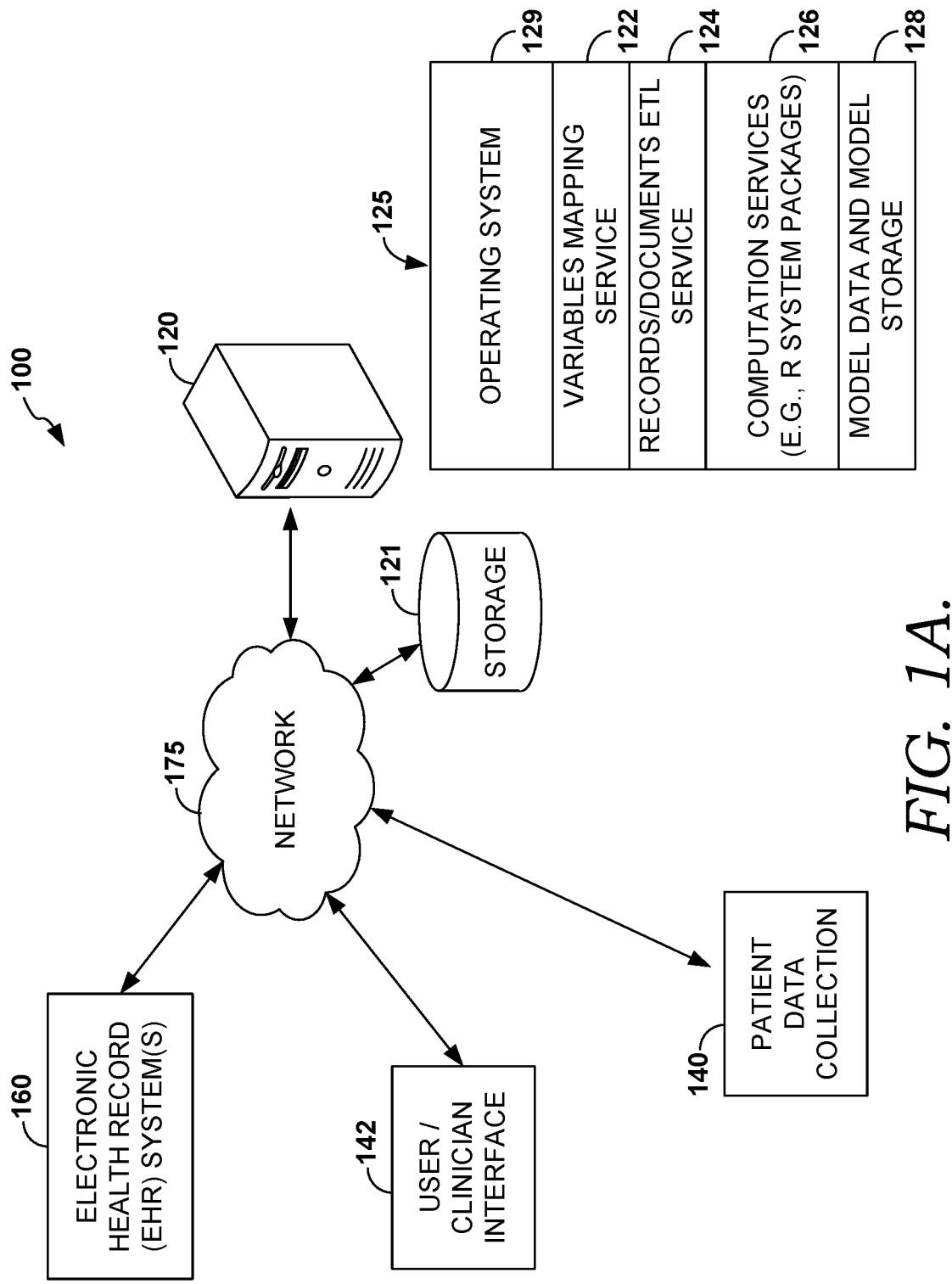
FIGS. 1A and 1B depict aspects of an illustrative architecture suitable for practicing an embodiment of the invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 100. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

As described above, system, methods, and computer-readable media are provided herein for early detection of the emergence of and reliable estimation of the likelihood of future significant macrophage activation syndromes, such as HLH. The treatment strategies recommended for acquired vs familial groups differ substantially. Usually treatment is initiated with dexamethasone 10 mg IV bid, cyclosporine 100 mg IV twice daily, anakinra 100 mg sc once daily, 1 dose of etoposide 100 mg IV, and optionally 3 rituximab infusions (range 1-10) at a median dose of 375 mg/m2, intravenous immunoglobulin (IVIG), and transfusions of blood products as needed to address the patient's cytopenias. To date, it is thought to be impossible to predict the HLH using conventional laboratory tests. HLH is characterized by excessive macrophage and T-cell activation as well as impairment of the ability of natural killer (NK) and cytotoxic T cells to kill target cells. Uncontrolled activation of T cells produces excess IL-2, tumor necrosis factor-alpha, and interferon-gamma. Recent studies show that serum levels of soluble interleukin-2 receptor (sIL2R) and ferritin are useful for differentiating some forms of HLH. However, these laboratory tests are not broadly available and are relatively expensive to perform even in those locations where they are available.

The main clinical features of HLH include high fever, hepatosplenomegaly, cytopenia of two or three of the cell lines in the bone marrow, and the presence of activated macrophages in hematopoietic sites; these constitute the classical HLH criteria. Among the two hemophagocytic syndrome subsets, primary/genetic or secondary/reactive, the latter is the most frequently seen in adults. This condition may be triggered by various underlying conditions such as infection (especially by Epstein-Barr virus (EBV), cytomegalovirus (CMV), or human immunodeficiency virus (HIV)), lymphoid malignancy (B- or T-cell lymphoma), connective tissue diseases, or some drugs. HLH criteria were established by the Histiocyte Society in 2004.

More recently, some have proposed an "HScore," a multi-variable diagnostic tool. Nine variables (3 clinical [i.e., known underlying immunosuppression, high temperature, organomegaly], 5 biologic [i.e., triglyceride, ferritin, serum glutamic oxaloacetic transaminase, and fibrinogen levels, cytopenia], and cytologic attributes [e.g., hemophagocytosis features on bone marrow aspirate]) are variables in the HScore. However, HScore and other conventional diagnostic methods are "lagging" indicators and do not positively identify HLH until it is well-established and relatively severe. Combinations of common laboratory parameters, such as the percentage of lymphocytes in the leukocyte differential cell count, elevated lactate dehydrogenase (LDH), elevated serum ferritin levels higher than 50,000 μg/L, and the sIL2R/ferritin ratio are useful for identifying patients with familial haemophagocytic lymphohistiocytosis and for differentiating the underlying etiology of pediatric HLH.

We have determined progressive pancytopenia is the feature most likely to suggest secondary HLH in the patients who develop shock and/or organ system failure. Use of other HLH-2004 diagnostic criteria is hindered by the poor operating characteristics of these tests in critically ill patients. Their usefulness is confounded by the facts that (a) treating physicians' therapeutic maneuvers substantially normalize many of the variables that are part of the HLH-2004 criteria, (b) necessary treatments for an underlying condition such as cancer produces abnormalities meeting the HLH-2004 criteria in a percentage of persons who do not later develop HLH, and (c) intercurrent infection or other comorbid conditions may partially mimic the features of macrophage activation syndromes, including HLH. Physical examination for splenomegaly and/or hepatomegaly similarly has poor statistical performance in terms of predictive accuracy. Bone marrow aspiration is presently the most useful diagnostic test, but frequently yields false-negative results. Additionally, due to its pain and invasiveness, bone marrow aspiration is not generally useful for longitudinal determination of progression or severity of macrophage activation and hemophagocytic syndromes.

For the foregoing reasons, the improved systems and methods provided by embodiments of this disclosure for ascertaining the presence of a macrophage activation syndrome and determining or predicting its severity in terms of acute probability of deterioration or organ system failure are valuable and needed. Further, the application of the embodiments described herein lead to a significant improvement in patient outcomes, clinical support systems, and the healthcare industry in general.

To achieve this improved system a first aspect described herein is directed to a method for predicting the occurrence of a macrophage activation syndrome in a human patient over a future time interval. The method includes receiving laboratory or physiologic measurement(s) of the patient and corresponding date-time coordinate(s), receiving previous measurement values and their respective measurement date-time coordinates, and receiving one or more predictive models previously determined from a population of patients in whom subsequent actual occurrences of a macrophage activation syndrome in a defined future time interval were known. Further, some embodiments include constructing a time series by appending the most recent value(s) to the previous series of measurements and determining that the length of the time series is at least three measurement members. For each member of the time series, the high-frequency components of a power spectrum or a surrogate measure of the high-frequency band of the power spectrum are calculated, thereby forming a set of parameters. A probability of a macrophage activation syndrome for the patient is determined by applying the parameters as inputs to the one or more predictive models. A calculated classification or probability of future macrophage activation syndrome occurrence within a future time interval is then determining for the patient. The calculated classification or probability is compared against a threshold and when the probability or classification exceeds the threshold the method emits a notification to a caregiver associated with the patient indicating the likelihood of an occurrence of a macrophage activation syndrome in an human patient over the future time interval.

A second aspect described herein is directed to a system for predicting the occurrence of a macrophage activation syndrome in a patient. Some embodiments of the system include an input means for entering at least one serial laboratory or physiologic measurements and at least one processing means communicatively coupled to the input means. The processing means may be configured to receive one or more laboratory or physiologic measurements or a patient and associated date-time coordinates, receive previous measurement values and their associated date-time coordinates, receive one or more predictive models previously determined from a population of patients in whom subsequent actual occurrences of a macrophage activation syndrome in a defined future time interval were known, construct at least one time series of the one or more laboratory or physiologic measurements, wherein the at least one time series comprises at least three measurement values and associated date-time coordinates, calculate, for each member of the at least one time series, high-frequency components of a power spectrum or a surrogate measure of the high-frequency band of the power spectrum thereby forming a set of parameters, determine a probability of a macrophage activation syndrome for the patient by applying the parameters as inputs to the one or more predictive models, wherein a generated output comprises a probability or classification, compare the calculated classification or probability against a threshold, determine that the probability or classification satisfies the threshold, and preform an action. In some embodiments the action may comprise at least one of notifying a responsible care provider, placing a new order in the patient's EMR, altering the patients care plan, reserving a resource, for the patient, in a care facility for treating macrophage activation disorder(s), modifying a plan of care for the patient that prevents interrupts, or delays discharge orders from being submitted or carried out, automatically scheduling increased monitoring of the patient; ordering increased testing of the patient, automatically scheduling a consultation with a specialist care provider, automatically issuing a clinical order for the patient, and issuing an electronic alert or notification to the responsible care provider or patient.

A third aspect described herein is directed to one or more computer storage media storing computer-useable instruction that, when implemented on a computing device, cause the computing device to perform operations. In some embodiments the operations may comprise receiving one or more laboratory and/or physiologic measurements of a patient and associated date-time coordinates; receiving previous measurement values and their associated date-time coordinates; receiving one or more predictive models previously determined from a population of patients in whom subsequent actual occurrences of a macrophage activation syndrome in a defined future time interval were known; constructing at least one time series of the one or more laboratory and/or physiologic measurement(s) by appending the recent measurement(s) to the previous measurement(s), wherein the at least one time series comprises at least three measurement values and associated date-time coordinates; calculating, for each member of the at least one time series, high-frequency components of a power spectrum or a surrogate measure of the high-frequency band of the power spectrum thereby forming a set of parameters; determining a probability of a macrophage activation syndrome for the patient by applying the parameters as inputs to the one or more predictive models, wherein a generated output comprises a probability or classification; comparing the calculated classification or probability against one or more thresholds; evoking an action corresponding to preparing for treatment of the patient based on comparing the probability to the one or more thresholds. In some embodiments, the action may be at least one of: notifying the responsible care provider; placing new order(s) in the patient's EMR; altering the patients care plan; reserving resources, for the patient, in the care facility needed to treat and/or manage the predicted macrophage activation disorder(s); preventing and/or interrupting discharge orders from being submitted for the patient until such time as a responsible care provider has disabled the automatic discharge prevention measure(s); ordering increased monitoring of the patient; ordering increased testing of the patient; ordering prescriptions for the patient; and/or issuing an electronic alert or notification to the a responsible care provider and/or patient.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, example operating environment 100 provides an aspect of a computerized system for compiling and/or running aspects of this disclosure, which in some embodiments may include collecting and analyzing unstructured text data from electronic health record(s), which may include claims data, to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

Operating environment 100 is one example of a suitable environment and system architecture for implementing an embodiment of the disclosure. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or FORTRAN. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or a plurality of EHR systems such as hospital EHR systems, health information exchange EHR systems, clinical genetics/genomics systems, ambulatory clinic EHR systems, psychiatry/neurology EHR systems, insurance, collections or claims records systems; and may be implemented in computer system 120. Similarly, EHR system 160 may perform functions for two or more of the EHR systems (not shown). In an embodiment, EHR system 160 includes historical claims data for health services, apportionment data, and related health services financial data.

In some embodiments of the disclosure, sequence itemset mining is performed using data about a population of patients derived from patient EHR information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system 160 include one or more data stores of health records, which may be stored on storage 121, and may further include one or more computers or servers that facilitate the storing and retrieval of the health records. In some embodiments, EHR system 160 may be implemented as a cloud-based platform or may be distributed across multiple physical locations. EHR system 160 may further include record systems, which store real-time or near real-time patient (or user) information, such as wearable, bedside, or in-home patient monitors or sensors, for example.

Example operating environment 100 further includes provider user/clinician interface 142 communicatively coupled through network 175 to an EHR system 160. Although environment 100 depicts an indirect communicative coupling between interface 142 and EHR system 160 through network 175, it is contemplated that an embodiment of interface 142 is communicatively coupled to EHR system 160 directly. An embodiment of interface 142 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet. A provider clinician application facilitates accessing and receiving information from a user or health care provider about a specific patient, set of patients, or provider clinicians, according to the embodiments presented herein. Embodiments of interface 142 also facilitates accessing and receiving information from a user or health care provider about a specific patient or population of patients including patient history; health care resource data; variables measurements, timeseries, and predictions (including plotting or displaying the determined outcome and/or issuing an alert) described herein; or other health-related information, and facilitates the display of results, recommendations, or orders, for example. In an embodiment, interface 142 also facilitates receiving orders for the patient from the clinician/user, based on the results of monitoring and predictions. Interface 142 may also be used for providing diagnostic services or evaluation of the performance of various embodiments.

As shown in example environment 100, user/clinician interface 142 is communicatively coupled through network 175 to EHR 160 and patient data collection 140. In an embodiment, patient data collection 140 communicates via network 175 to computer 120 and/or provider clinician interface 142. In an embodiment of patient data collection 140 (sometimes referred to herein as patient monitor or patient measuring device) comprises one or more sensor components operable to receive or acquire clinical or physiological information about a patient, such as various types of physiological measurements, physiological parameters or variables, or similar clinical information associated with a particular physical or mental state of the patient, and which may be acquired periodically or as one or more time series. In an embodiment, one or more sensor components of patient data collection 140 may comprise a user-wearable sensor component or sensor component integrated into the patient's environment. Examples of sensor components of such embodiment of patient data collection 140 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about patient, such as the monitored parameters or variables and/or clinical narratives regarding the patient, used according to the embodiment of the invention disclosed herein may be received from human measurements, human observations, or automatically determined by sensors in proximity to the patient. For example, in one embodiment, a nurse periodically measures a patient's physiological variables, such as blood pressure or other variables described herein, and enters the measurement and/or observations via patient data collection 140 or interface 142. In another example, a nurse or caregiver enters one or more progress notes for an in-patient via patient data collection 140 or interface 142.

Examples of physiological parameters or variables received via patient data collection 140 can include, by way of example and not limitation, heart rate, blood pressure, oxygen saturation (SoO2), central venous pressure, other vital signs, other laboratory or physiological parameters described herein, or any type of measureable, determinable, or observable physiological or clinical variable or characteristic associated with a patient, which in some embodiments may be used for forecasting a future value (of the measured variable, a composite variable based on one or more measured variables, or other factor determined at least in part from one or more measured variables) of a patient in order to facilitate clinical decision making For example, in some embodiments, patient data collection 140 may be used for acquiring, determining, or characterizing (by a human caregiver) other types physiological variables such as, muscle activity which might be sensed from electromyogram signals, eye movement which might be sensed from electro-oculogram signals, or other biometric information. In an embodiment, patient monitor 140 collects raw sensor information and performs signal processing, such as velocity measurement, forming a physiological variable decision statistic, cumulative summing, trending, wavelet processing, thresholding, computational processing of decision statistics, logical processing of decision statistics, pre-processing or signal condition, etc., part or all of which may be performed on patient data collection 140, interface 142, and/or computer system 120.

Example operating environment 100 further includes computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on interface 142. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interfaces 140 and 142. In some embodiments, interface 142 operates in conjunction with software stack 125.

In embodiments, variables mapping service 122 and records/documents ETL service 124 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages such as packages fractal, for fractal time series modeling and analysis, and entropy, which includes various estimators for determining entropy, or similar program routines or libraries. Computation services 126 also may include natural language processing services (not shown) such as Discern nCode™ developed by Cerner Corporation, or similar services. In an embodiment, computation services 126 include the services or routines, which may be embodied as one or more software agents or routines such as the example embodiments of computer program routines illustratively provided in FIG. 6A. In some embodiments, computation services 126 use EHR 160 and/or model data and model storage services 128. Some embodiments of stack 125 may further use Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores frequent events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
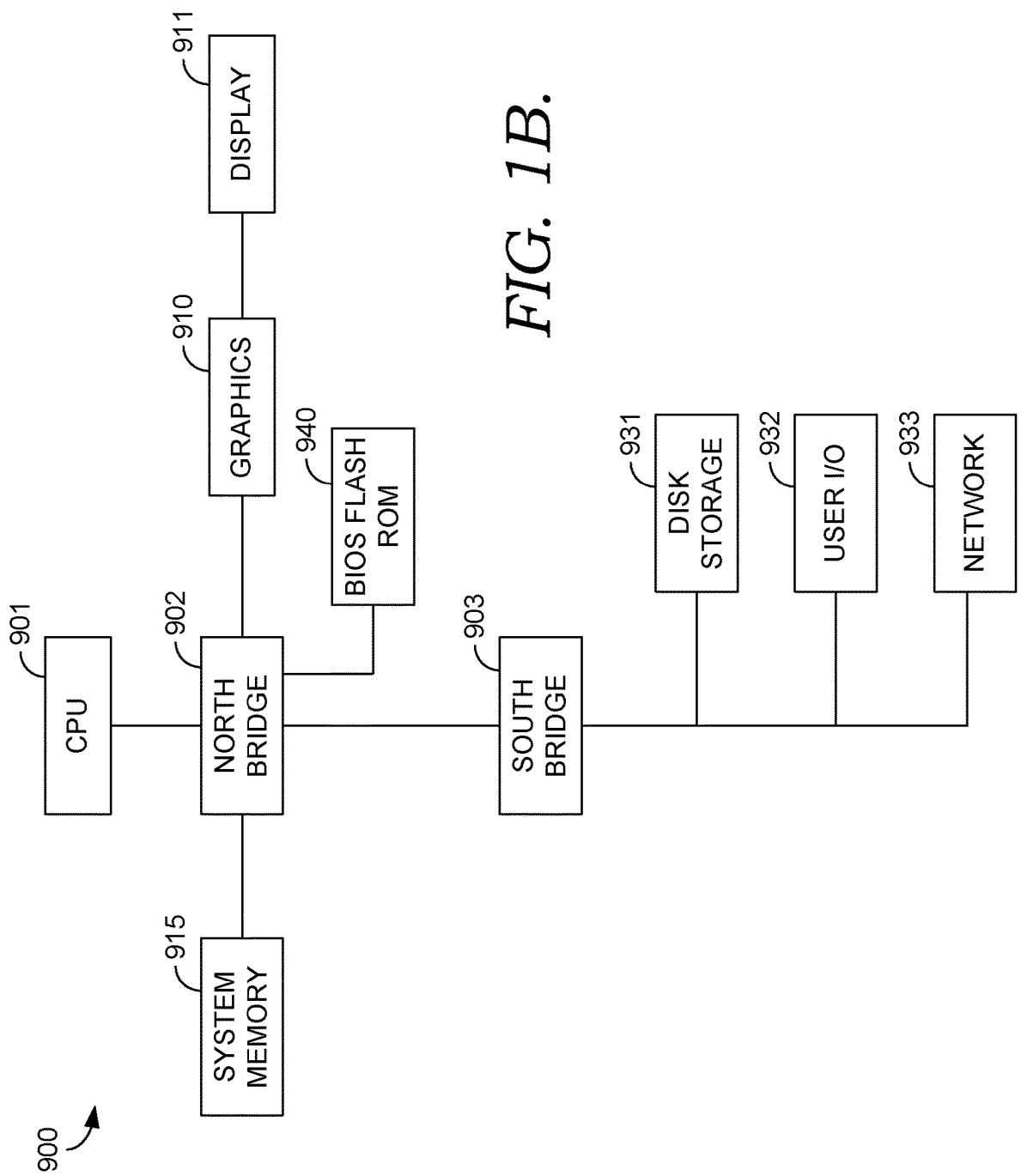

Turning briefly now to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2A:
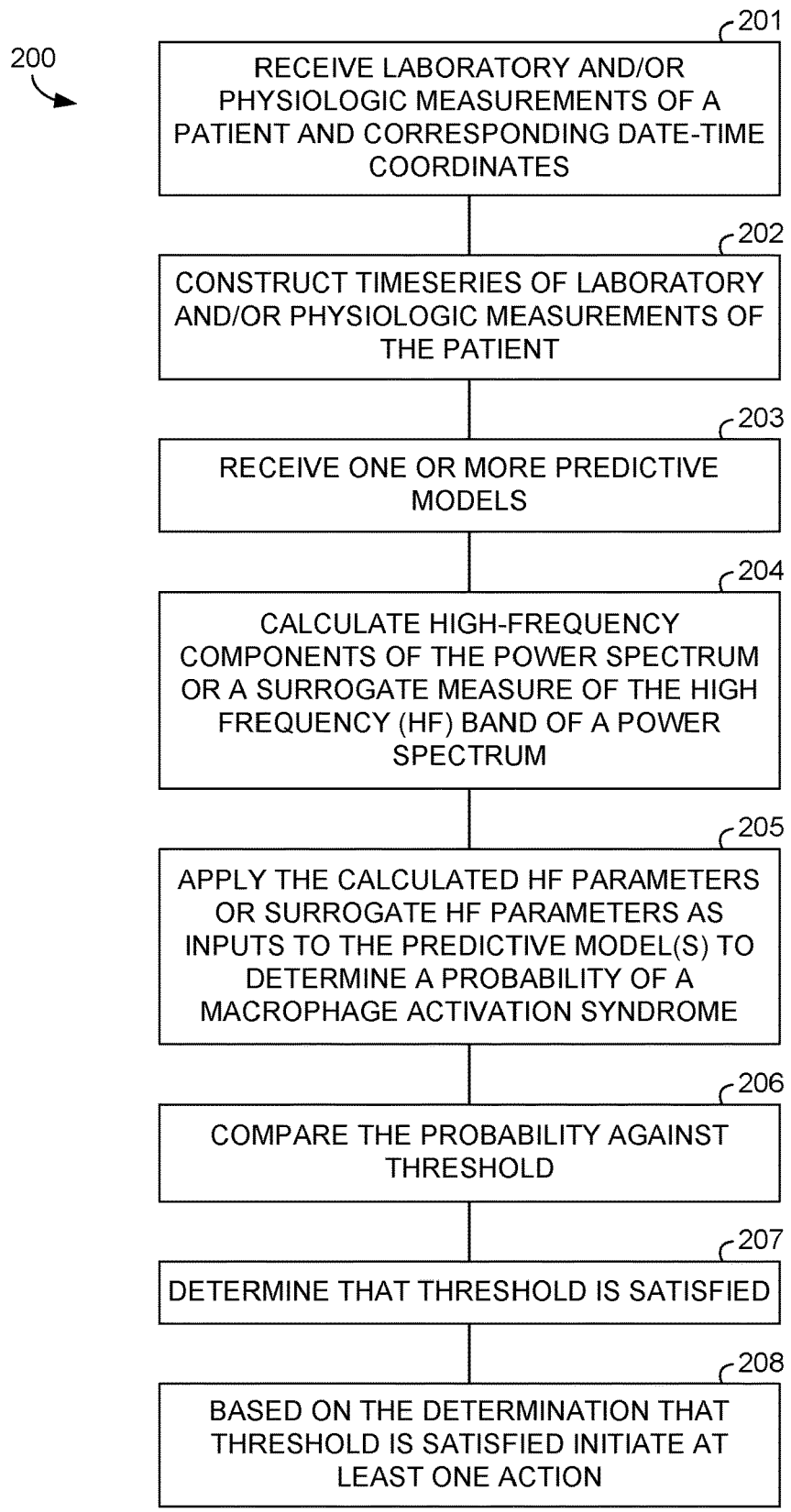
FIGS. 2A and 2B depict a flow diagram of an exemplary method for generating one or more gradient boosting models for use in determining or predicting the occurrence of a macrophage activation syndrome, in accordance with an embodiment of this disclosure.

With reference now to FIG. 2A, an exemplary method 200 is provided for generating one or more gradient boosting models for use in determining or predicting the occurrence of a macrophage activation syndrome. Embodiments of method 200 implement the discovery that a characteristic aspect of macrophage activation disorders, including HLH, entails increased high-frequency variability of various laboratory biomarkers and physiological measurements, reflecting altered dynamics and homeostatic control of interrelated physiologic and biologic subsystems. Some embodiments of portions of method 200 may be performed using the computer program routine illustratively shown in FIG. 6A and may use a model probability lookup table such as the example depicted in FIG. 6B.

In an embodiment of method 200 a series of a single laboratory biomarker and/or physiologic measurement may be used. For example, heart rate, systolic blood pressure, ferritin, fibrinogen, LHD, triglyceride, erythrocytes, leukocytes, platelets, albumin, lactate dehydrogenase, creatinine, resting respiratory rate, resting heart rate, or body temperature measurements may be used. It will be understood by those skilled in the art that the prior example is not an exhaustive list of the laboratory biomarker or physiologic measurements contemplated by the disclosed invention; rather, it is merely an illustrative example and, as such, any laboratory biomarker and/or physiologic measurements may be used in an embodiment of method 200 without departing from the scope of this disclosure.

In an embodiment of method 200, a series of at least two laboratory biomarkers and/or physiologic measurements may be used. For example, at least two of heart rate, systolic blood pressure, ferritin, fibrinogen, LHD, triglyceride, erythrocytes, leukocytes, platelets, albumin, lactate dehydrogenase, creatinine, resting respiratory rate, resting heart rate, and/or body temperature measurements may be used. It will be understood by those skilled in the art that the prior example is not an exhaustive list of the laboratory biomarker or physiologic measurements contemplated by the disclosed invention; rather, it is merely an illustrative example and, as such, any laboratory biomarker and/or physiologic measurements may be used in an embodiment of method 200 without departing from the scope of this disclosure.

At step 201, receive laboratory and/or physiologic measurements of the patient and corresponding date-time coordinates. In an embodiment, step 201 comprises measuring (or receiving) the most recent laboratory in physiologic measurement(s) and corresponding date time coordinate(s). Embodiments of step 201 may be facilitated using patient data collection component 140. Additionally, and/or alternatively, an embodiment of step 201 may be facilitated by using EHR 160 and/or any electronic health record communicatively coupled with network 175. As such, an embodiment of step 201 may access/receive laboratory and/or physiologic measurements of the patient from healthcare facilities, and/or laboratories, other than the healthcare facility where the patient is currently located. For example, the most recent laboratory or physiologic measurement and corresponding date time coordinate may be a laboratory or physiologic measurement taken by the patient's primary care physician at the primary care physician's office and stored in the primary care physician's electronic health record system. At some later point in time, the patient may be admitted to a hospital wherein an embodiment of method 200 may be performed. At step 201, the laboratory or physiologic measurement(s) stored in the primary care physicians electronic health record system may be accessed through network 175.

At step 202, construct a time series of laboratory and/or physiologic measurements of the patient. The time-series may comprise previous measurement values and their respective measurement date-time coordinates, and may be received from an operational data store, such as storage 121. Some embodiments of step 202 further comprise constructing a time series by appending the most recent measurement values determined in step 201 to the previous time series retrieved in step 202 thereby forming an updated time series.

In an embodiment, step 202 further comprises determining that the time-series is of sufficient length for the determination of the probability of macrophage activation syndrome. In such an embodiment, when the length of the time series is determined to be of sufficient length the method 200 continues to step 203. Otherwise method 200 waits until the next measurement (step 201) is received and appended to the time series, thereby lengthening it. In an embodiment of step 202, the method 200 continues to wait, receive, and append measurements until such time as a time-series of sufficient length is created.

In an embodiment of step 202, the time-series is of sufficient length when it comprises at least two measurements. In an embodiment, the time series is of sufficient length when it comprises at least three measurements in length. In an embodiment, the time-series comprises at least three measurements acquired at, at least, 24 hour intervals. As such, a first measurement may be acquired at $T_0$, a second measurement may be acquired at $T_1$, wherein $T_1 \geq T_0 + 24$ hours. A third measurement may be acquired at $T_2$, wherein $T_2 \geq T_1 + 24$ hours. Additionally, in an embodiment, measurements acquired between the 24 hour intervals may be included in the time series so long as at least three measurements are acquired with, at least, 24 hour between measurements. For example, the first measurement may be acquired at $T_0$; $n_0$ measurement(s) may be acquired between $T_0$ and $T_1$; the second measurement may be acquired at $T_1$, $n_1$ measurement(s) may be acquired between $T_1$ and $T_2$; and, the third measurement may be acquired at $T_2$. As such, the time series may include at least the first measurement, $n_0$ measurement(s), the second measurement, $n_1$ measurement(s), and the third measurement.

Additionally, and/or alternatively, in an embodiment, the time intervals between measurements may be the same duration or may be of varying duration. In an embodiment, the three or more measurements may be acquired within thirty days (e.g., $T_0$, $T_1$, and $T_2$ occur within thirty days).

Additionally, in some embodiments, the measurements for a given laboratory or physiologic parameter may be acquired, at least in part, asynchronously from other laboratory or physiologic parameters. For example, measurements for a first parameter may be acquired over a first time period; measurements for a second parameter may be acquired over a second time period; measurements for a third parameter may be acquired over a third time period; and, measurements for a fourth parameter may be acquired over a fourth time period. It will be understood by those skilled in the art that the various time periods may overlap, include individual measurements from the same specimen, or may be identical. As such, embodiments of the disclosure are not reliant on laboratory or physiological measurements made at the same time or with the same patient specimen.

At step 203, receive one or more predictive models. In an embodiment, the predictive model(s) is generated and trained from a population of patients in whom subsequent actual occurrences of macrophage activation syndrome in a defined future interval are known, as further described herein. In some embodiments, the models may be stored and received from a reference data store, which may be embodied as storage 121 and/or model data and models storage services 128. Similarly, in an embodiment of step 203, method 200 may receive an indication that the one or more predictive models is available for use and in turn prepare the one or more time series for transmission. In other words, an embodiment of step 203 may receive an indication that one or more predictive models "housed" in a communicatively coupled specially configured computer, is available to receive the patient data (e.g. has computational capacity available). In such an embodiment, step 203 may further comprise securely transmitting the patient data to the one or more predictive models for remote analysis.

At step 204, calculate high-frequency components of a power spectrum or a surrogate measurement of the high frequency band of a power spectrum. Embodiments of step 204 calculate high-frequency components of the power spectrum of each of the one or more time-series, constructed at step 202, or a surrogate measure of the high-frequency band of the power spectrum, such as the root mean square of successive deviations (RMSSD) of each of the one or more time series, constructed at step 202. In some embodiments, step 204 may be facilitated by computation services 126.

At step 205, apply the calculated high-frequency parameters or surrogate high-frequency parameters, calculated at step 204, as inputs to the predictive model(s), received at step 203, to determine the forecast probability of current and/or future macrophage activation disorders for the patient. Embodiments of step 205 may calculate the forecast probabilities of a macrophage activation syndrome, such as HLH, by applying the parameters above as inputs to predictive model(s) previously determined from a population of patients in whom subsequent actual occurrences of a macrophage activation syndrome such as HLH in a defined future time interval were known. In some embodiments, the calculated high-frequency parameter or surrogate high-frequency parameter, from step 204, and the one or more time series, from step 202, may be applied as inputs to the predictive model(s) to determine the forecast probability of current and/or future macrophage activation disorders for the patient. In some embodiments, the calculated high-frequency parameter or surrogate high-frequency parameter from step 204 may be applied as inputs to the predictive model(s) to determine the forecast probability of current and/or future macrophage activation disorders for the patient. Using the model(s) updated with input parameters, a calculated classification and/or forecast probability of future macrophage activation syndrome occurrence within the defined future time interval is determined. In some embodiments, step 203 may use the computer program routine illustratively shown in FIG. 6A and/or may use a model probability lookup table such as the example depicted in FIG. 6B.

Figure 6B:
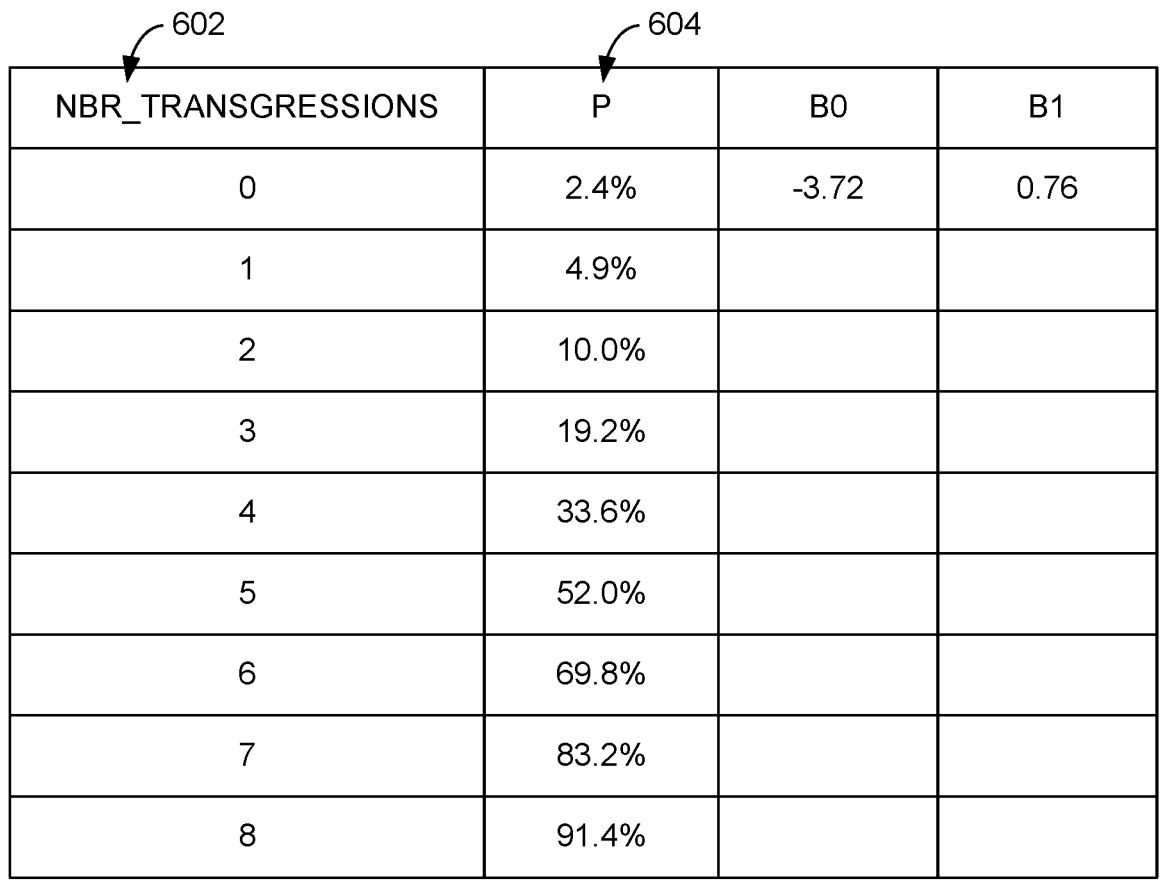
FIG. 6B depicts a look-up table of probabilities utilized by the example predictive model, in accordance with an embodiment of this disclosure.

Turning briefly to FIG. 6B, an exemplary model probability lookup table is provided. In embodiments, this example lookup table may include the number of transgressions 602 detected by the predictive model(s), for example as shown in the computer program routine shown in FIG. 6A. In embodiments the number of transgressions 602 may be associated with a forecast probability 604.

Returning to FIG. 2A, at step 206 compare the probability against a threshold. Some embodiments of step 206 compare the calculated classification and/or forecast probability calculated at step 205 to a threshold. The forecast probability may be compared to one or more threshold probabilities, at step 206. The threshold probabilities may be predetermined by a medical professional or medical care provider or be empirically based. In an embodiment of step 206, the threshold may be a predetermined probability and/or classification. Additionally, in an embodiment of step 206 the threshold may be a predetermined probability and/or classification determined based on the patient's underlying condition(s) and/or the laboratory or physiologic measurements used to construct the time-series. For example, a threshold probability may be established at one value for patients with cancer; a threshold probability maybe established at a second value for patients with an infectious disease; a threshold probability maybe established at a third value for patients with cancer and a comorbid infectious disease; and/or, a threshold probability maybe established at a fourth value for patients with an autoimmune disease. For another example, a threshold probability maybe established for probabilities calculated based on of a first laboratory or physiological parameter (e.g., ferritin); a threshold may be established for probabilities calculated based on of a second laboratory or physiologic parameter (e.g., fibrinogen); a threshold may be established for probabilities based on of a third laboratory or physiologic parameter (e.g., heart rate); and so on. For yet another example, a threshold may be established for probabilities calculated based on various combinations of two or more laboratory or physiologic parameters. It will be understood by those skilled in the art that the above referenced examples represent an illustrative subset of possible predetermined thresholds and as such are not intended to limit the scope of this disclosure.

At step 207, determine that the probability threshold is satisfied. In some embodiments, the probability threshold may be satisfied when, for example, the forecast probability exceeds the threshold probability. In some embodiments, the probability threshold may be satisfied when, for example, the forecast probability equals the threshold probability.

At step 208, based on the determination that the threshold is satisfied, initiate at least one action. Embodiments of step 208, implement method 200 in a tangible way by using the results of, at least, step 207 to initiate at least one action. In an embodiment, the action may be notifying the responsible care provider; placing new order(s) in the patient's EMR; altering the patient's care plan; reserving resources, for the patient, in the care facility needed to treat and/or manage the predicted macrophage activation disorder(s); preventing and/or interrupting discharge orders from being submitted for the patient until such time as a responsible care provider has reviewed method 200's results and disabled the automatic discharge prevention measure(s); ordering increased monitoring of the patient; ordering increased testing of the patient; and/or ordering prescriptions for the patient; issuing an electronic alert or notification to the a responsible care provider and/or patient.

Further it will be understood that embodiments of method 200 may include additional and/or alternative steps; like those discussed in relation to method 209.

Figure 2B:
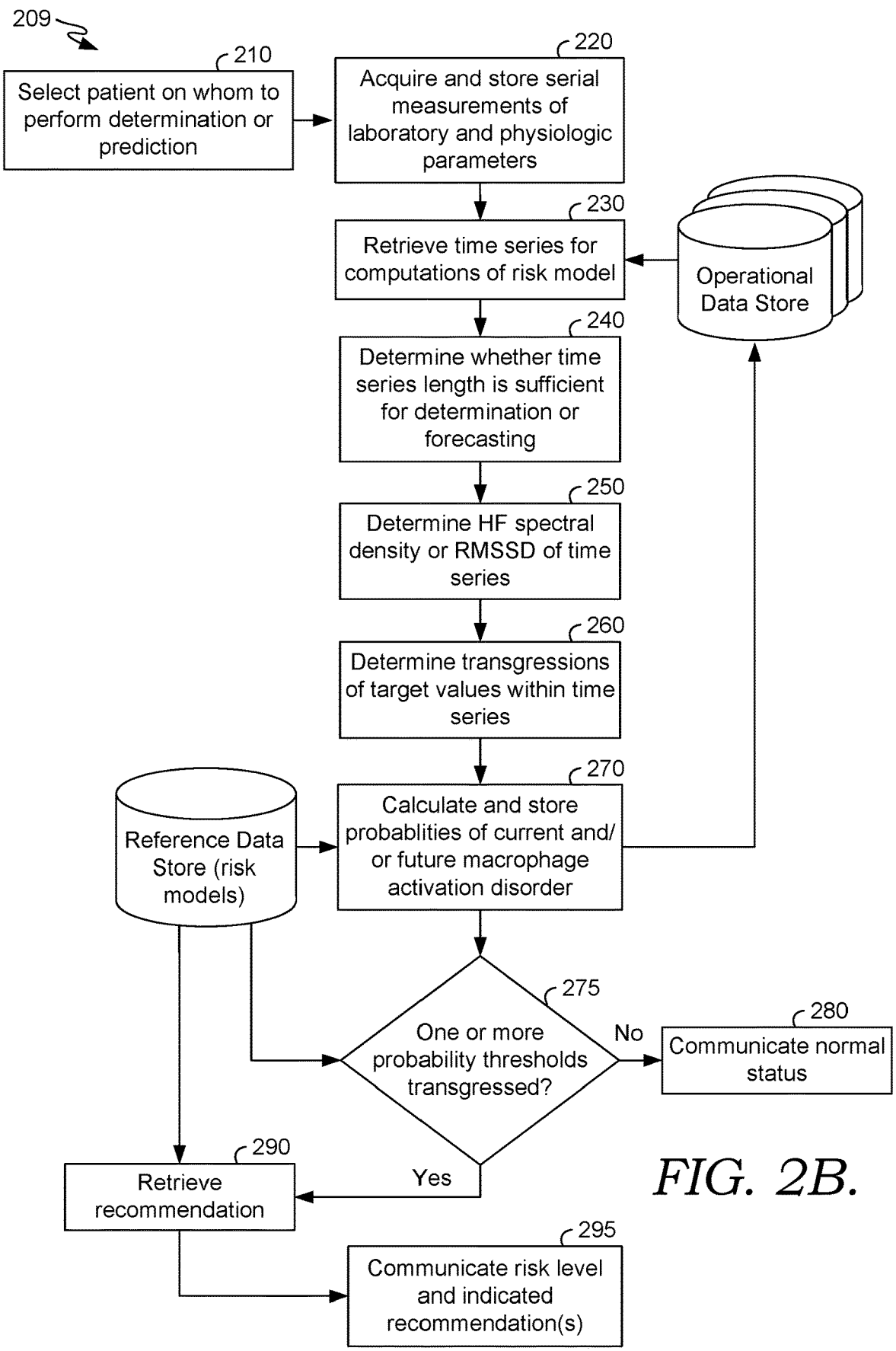
Figure 3A:
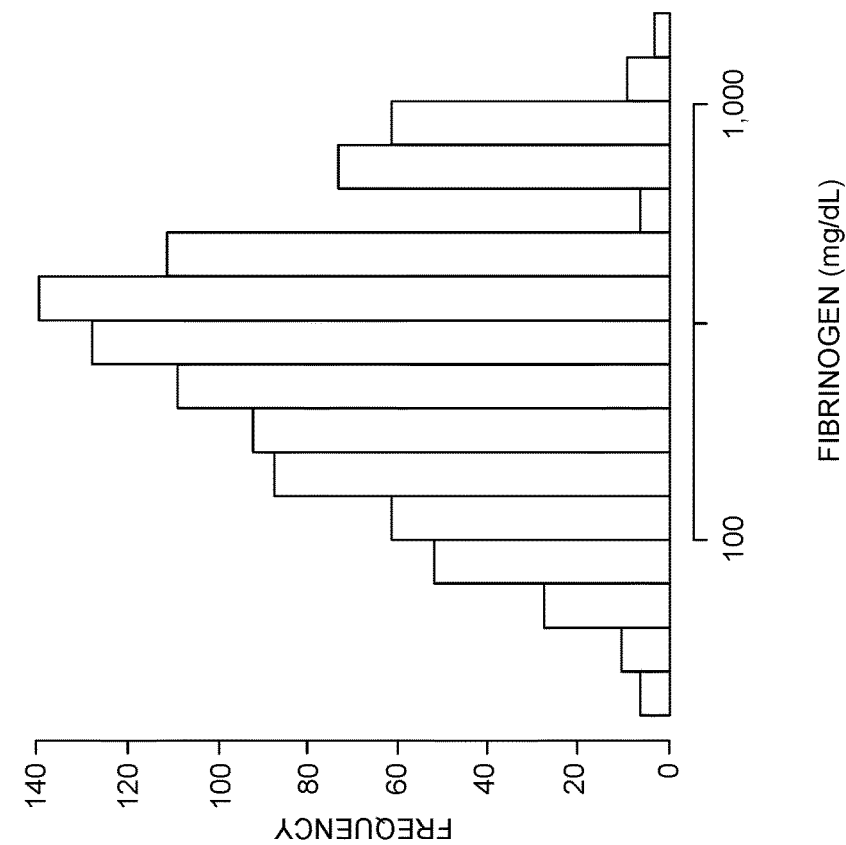
FIGS. 3A-3D depict statistical distributions of values of the root mean square of successive differences for a 3-sample-wide time series for one of the laboratory parameters used for determining predictive models for HLH, in an embodiment of this technology reduced to practice.
Figure 3B:
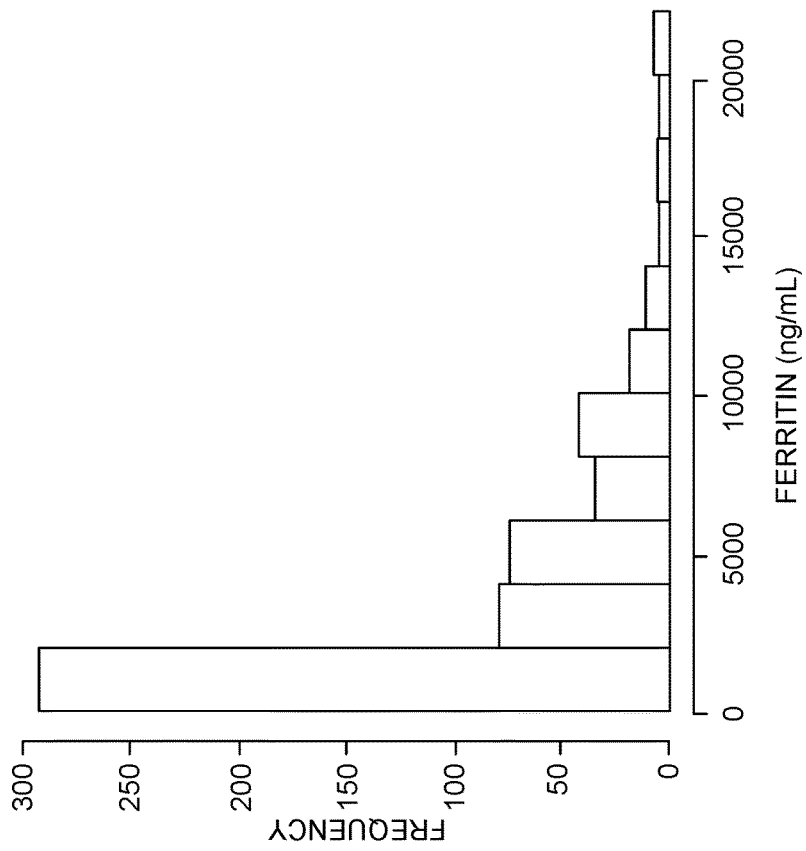
Figure 3D:
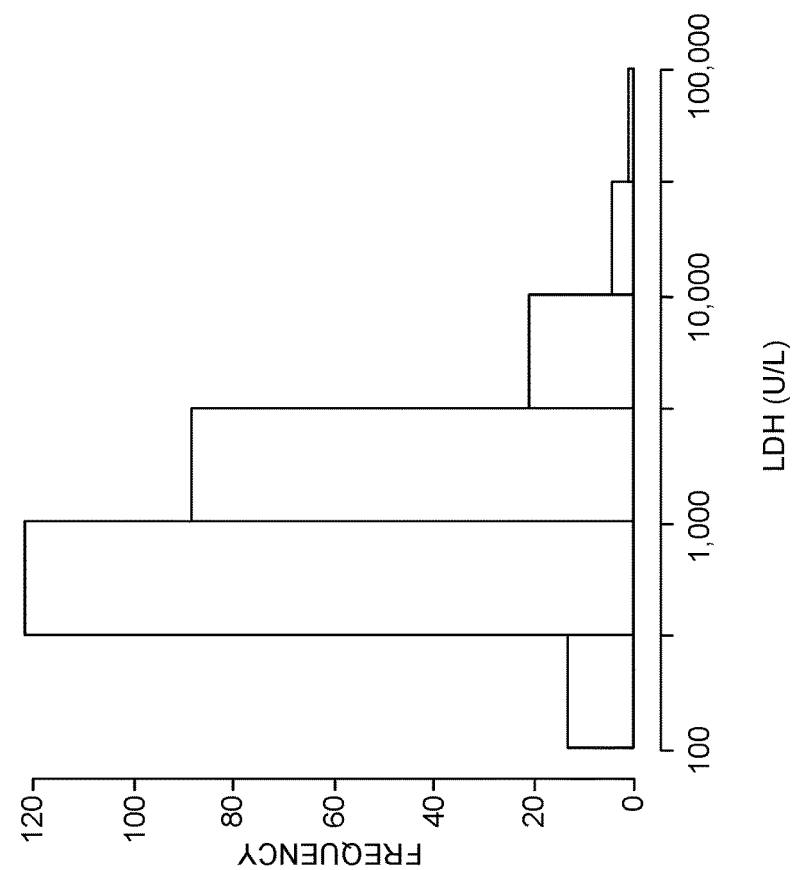
Figure 3C:
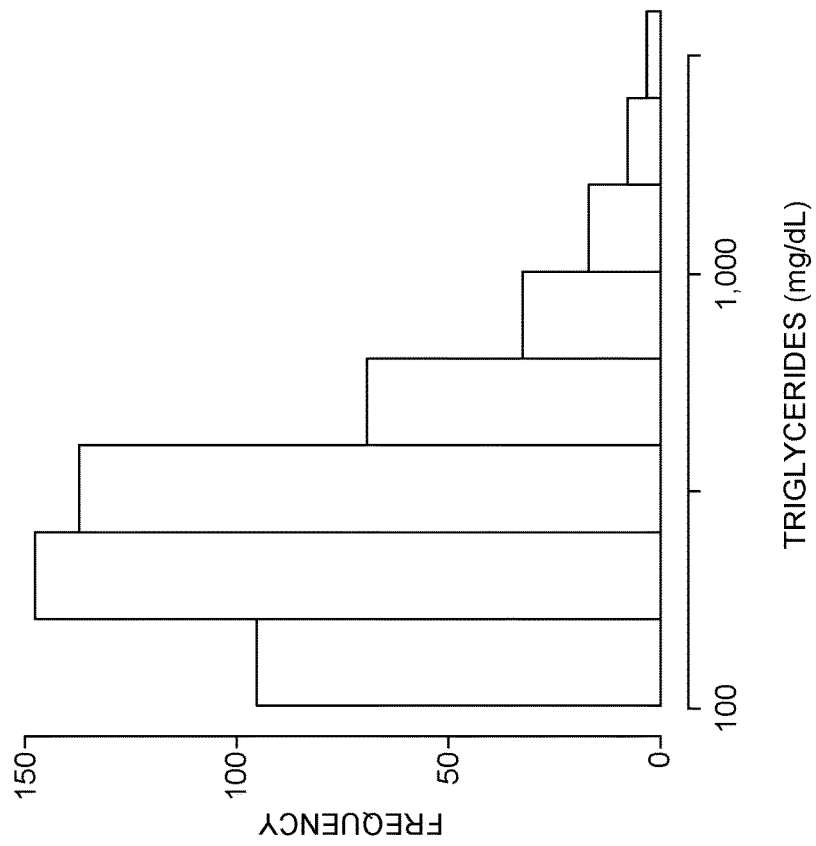
Figure 4A:
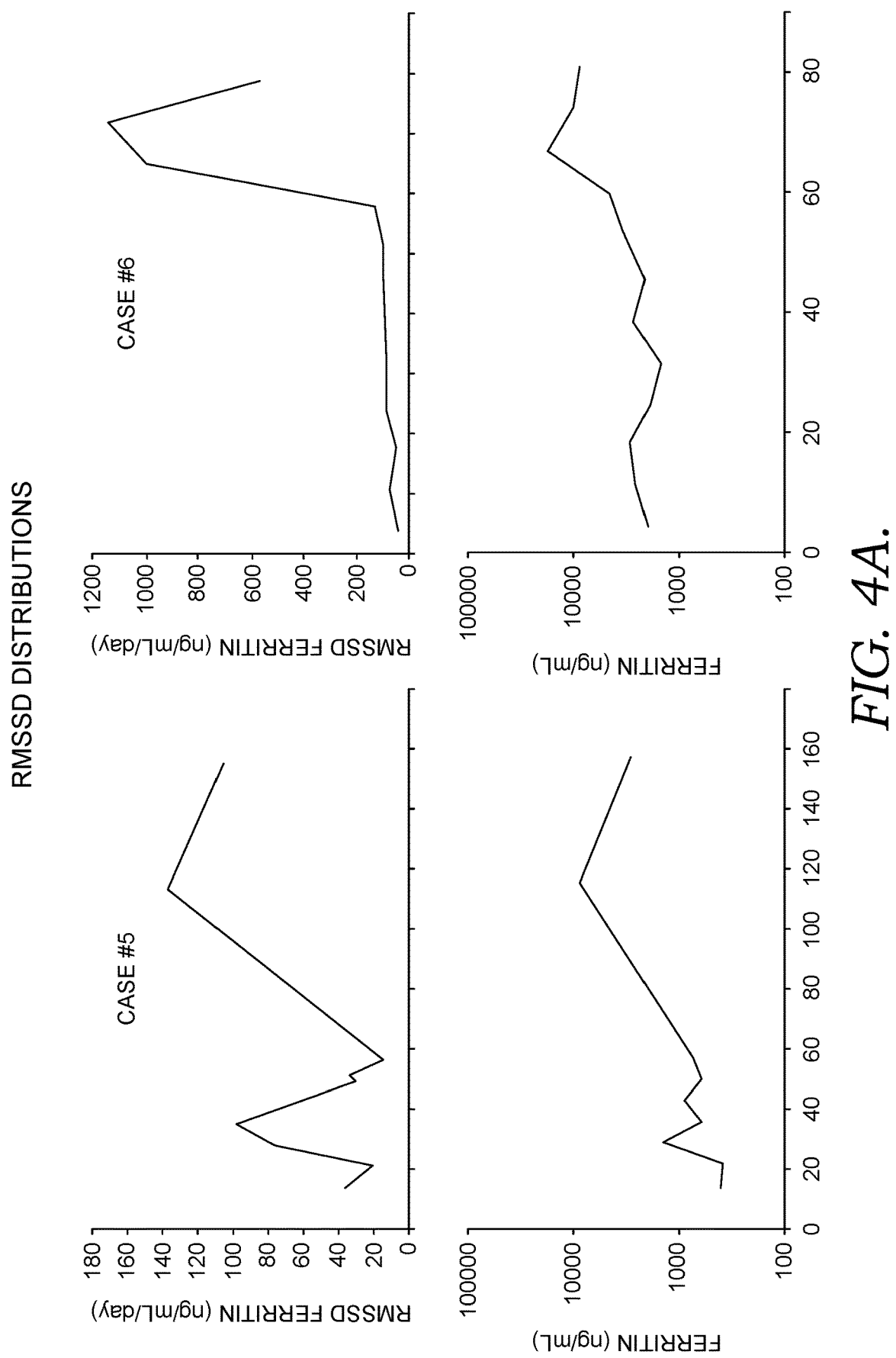
FIGS. 4A-4D depict root mean square of successive deviations (RMSSD) distributions from an embodiment of this technology reduced to practice.
Figure 4B:
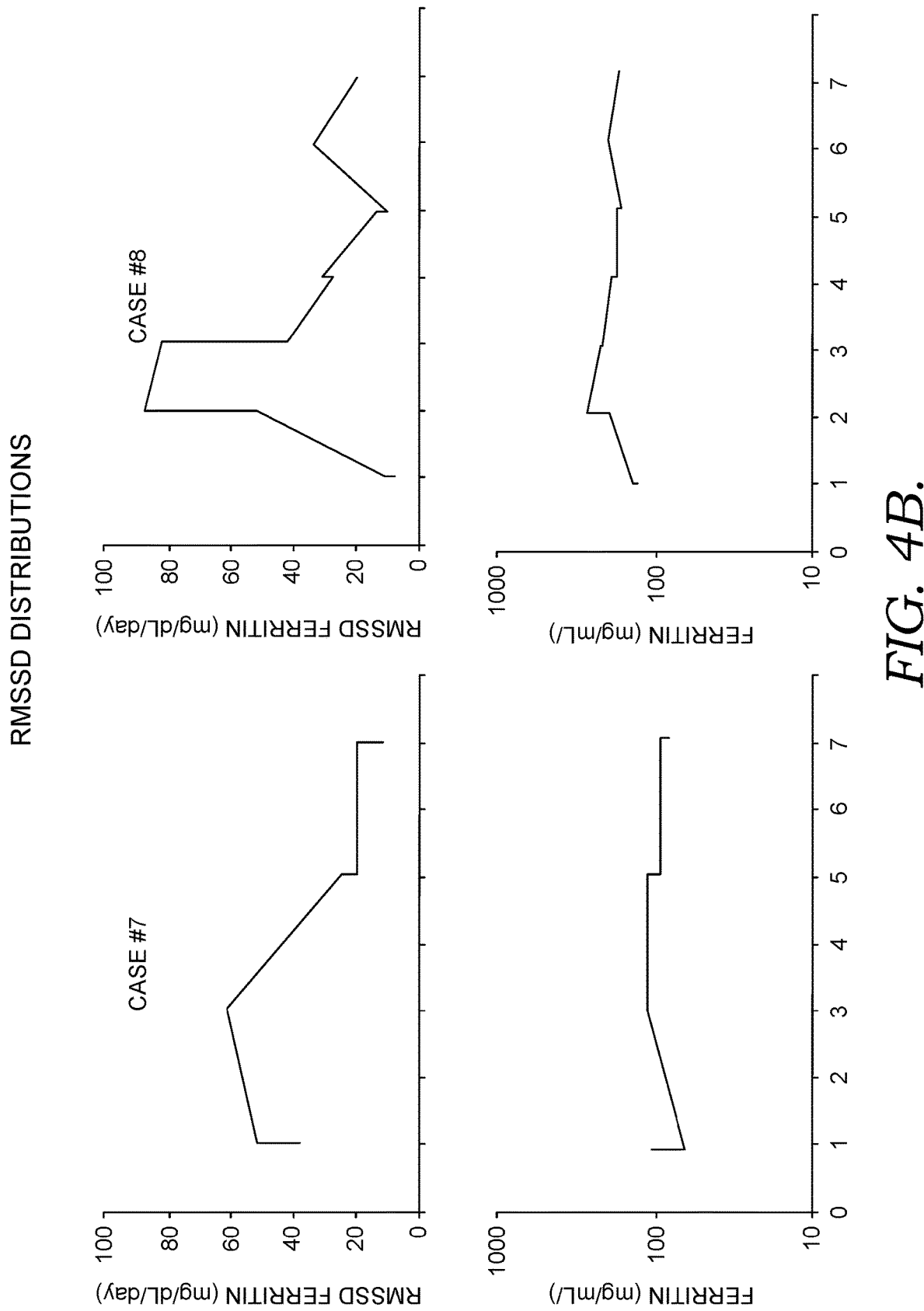
Figure 4C:
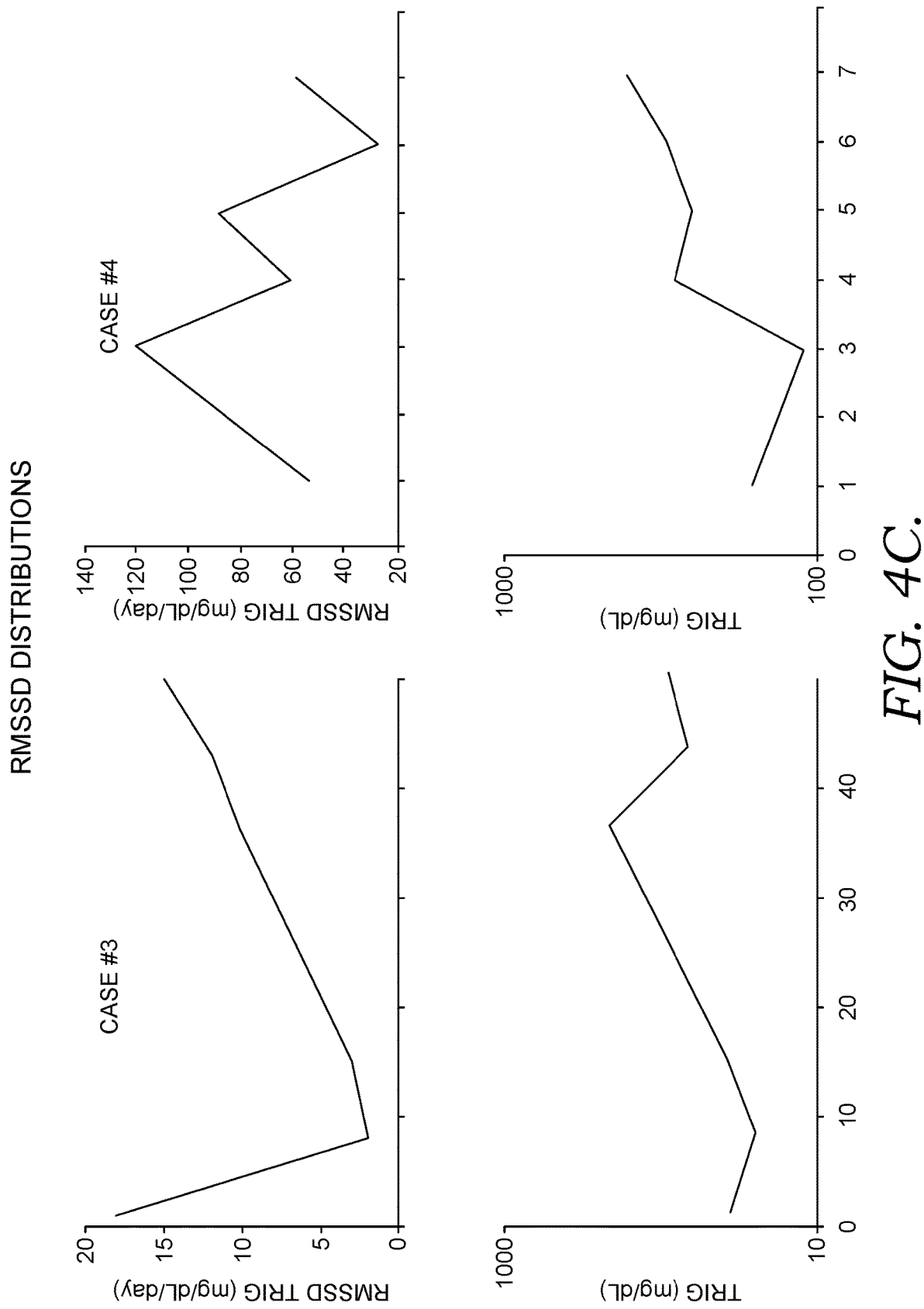
Figure 4D:
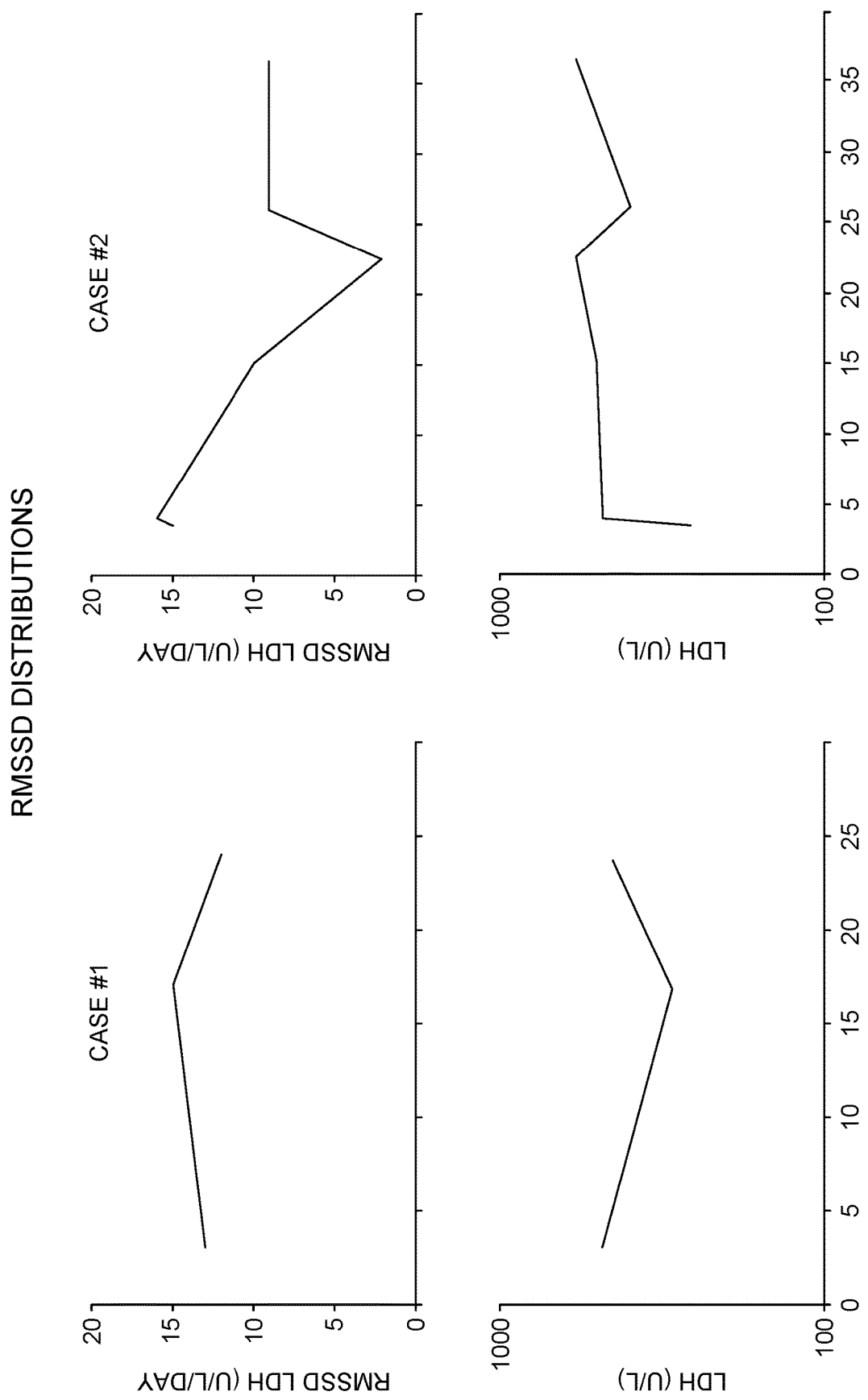

With reference now to FIG. 2B, a flow diagram is provided illustrating an exemplary method 209 for generating one or more gradient boosting models for use in determining or predicting the occurrence of a macrophage activation syndrome. Embodiments of method 209 implement the discovery that a characteristic aspect of macrophage activation disorders, including HLH, entails increased high-frequency variability of various laboratory biomarkers and physiologic measures, reflecting altered dynamics and homeostatic control of interrelated physiologic and biologic subsystems. Some embodiments of portions of method 209 may be performed using the computer program routine illustratively shown in FIG. 6A and may use a model probability look-up table such as the example depicted in FIG. 6B. Some embodiments of method 209 and/or some portions of method 209 may be facilitated by environment 100.

In an embodiment of method 209 a series of a single laboratory biomarker and/or physiologic measurement may be used. For example, heart rate, systolic blood pressure, ferritin, fibrinogen, LHD, or triglyceride measurements may be used. It will be understood by those skilled in the art that prior example is not an exhaustive list of the laboratory biomarker or physiologic measurements contemplated by the disclosed invention; rather, it is merely an illustrative example and as such any laboratory biomarker and/or physiologic measurements may be used in an embodiment of method 209 without departing from the scope of this disclosure.

In an embodiment, a series of at least two laboratory biomarkers and/or physiologic measurements may be used. For example, at least two of heart rate, systolic blood pressure, ferritin, fibrinogen, LHD, and triglyceride measurements may be used. It will be understood by those skilled in the art that prior example is not an exhaustive list of the laboratory biomarker or physiologic measurements contemplated by the disclosed invention; rather, it is merely an illustrative example and as such any laboratory biomarker and/or physiologic measurements may be used in an embodiment of method 209 without departing from the scope of this disclosure.

At step 210, determine the patient on whom to perform the macrophage activation syndrome determination or prediction. In an embodiment, the determination may be made automatically based off of predetermined criteria, a rule, a rule set, a machine learned model, a predictive algorithm, and/or the like. As such, an embodiment of method 209 may be used as a pervasive screening tool. For example, at step 210 the system may determine it appropriate to perform macrophage activation syndrome determination or prediction on the entire patient population, or a subpopulation, of a hospital at set intervals, continuously, or as the requisite patient measurements are acquired. For another example, step 210 may use patient information such as patient demographics, diagnosis, care plans, medications, or the like to determine whom to perform the macrophage activation syndrome determination or prediction on. In an embodiment, the determination may be made by a user/clinician through the user/clinician interface 142. As such, an embodiment of method 209 may be used to enhance decision support systems and health care networks to function as a targeted screening or prediction tool.

At step 220, acquire and store serial measurements of laboratory and physiologic parameters. In one embodiment, step 220 comprises measuring (or receiving) the most recent laboratory and physiologic measurement(s) and corresponding date-time coordinate(s). Embodiments of step 220 may be facilitated using patient data collector 140. Additionally, and/or alternatively, embodiments of step 220 may be facilitated by using EHR 160.

At step 230, retrieve time series from previous measurements to use for computation of risk model. The time series may comprise previous measurement values and their respective measurement date-time coordinates, and may be received from an operational data store, such as storage 121. Some embodiments of step 230 further comprise constructing a time series by appending the most recent measurement values determined in step 220 to the previous time series retrieved in step 230 thereby forming an updated time series.

At step 240, the length of the time series is determined and if the length is sufficient, then method 209 continues to step 250. Otherwise, method 209 waits until the next measurement (step 220) is received and appended to the time series, thereby lengthening it. In an embodiment, the time series is at least three measurements in length before proceeding to step 250 for further calculation of forecasts, beginning with computation of the input values required by the statistical predictive models.

As discussed in reference to step 202, in an embodiment of step 240 the time series comprises at least three measurements acquired at, at least, 24 hour intervals. Again as discussed in reference to step 202, in an embodiment of step 240 measurements acquired between the 24 hour intervals may be included in the time series so long as at least three measurements are acquired with, at least, 24 hour between measurements.

Again as discussed in reference to step 202, in an embodiment of step 240 the time intervals between measurements may be the same duration or may be of varying duration. In an embodiment, the three or more measurements are acquired within thirty days (e.g., $T_0$, $T_1$, and $T_2$ occur within thirty days). It will be understood by those skilled in the art that, as discussed above, the time series may comprise previously acquired measurements without departing from the scope of the invention.

Additionally, in some embodiments, the measurements for a given laboratory or physiologic parameter may be acquired, at least in part, asynchronously from other laboratory or physiologic parameters. For example, measurements for a first parameter may be acquired over a first time period; measurements for a second parameter may be acquired over a second time period; measurements for a third parameter may be acquired over a third time period; and, measurements for a fourth parameter may be acquired over a fourth time period. It will be understood by those skilled in the art that the various time periods may overlap, include individual measurements from the same specimen, or may be identical. As such, embodiments of the disclosure are not reliant on laboratory or physiological measurements made at the same time or with the same patient specimen.

At step 250, determine high frequency spectral density or root mean square of successive deviations of the time series. Embodiments of step 250 calculate high-frequency components of the power spectrum of each of the time series, or a surrogate measure of the high-frequency band of the power spectrum, such as the root mean square of successive deviations (RMSSD) of each of the time series. At step 260, in some embodiments, method 209 determines the transgressions of target values within the time series.

At step 270, calculate and store the probabilities of current and/or future macrophage activation disorder for the patient. Embodiments of step 270 may calculate the probabilities of a macrophage activation syndrome, such as HLH, by applying the parameters above as inputs to predictive models previously determined from a population of patients in whom subsequent actual occurrences of a macrophage activation syndrome such as HLH in a defined future time interval were known. The models may be stored and received from a reference data store, which may be embodied as storage 121. Using the models updated with input parameters, a calculated classification or forecast probability of future macrophage activation syndrome occurrence within the defined future time interval is determined.

At step 275, it is determined whether one or more probability thresholds is satisfied. Embodiments of step 275 determine whether the forecast probabilities or classifications received exceed the probability threshold(s) established for issuing an alarm or other signal to the patient or to the patient's caregivers, or performing another action. In some embodiments, the thresholds are pre-determined, may be determined based on the particular condition (e.g., HLH), or determined based on the patient, including physiological or demographics information about the patient. In some embodiments of step 275, the probability threshold is determined as discussed in reference with step 206.

If the threshold(s) are not transgressed, then method 209 proceeds to step 280, and information is provided indicating that the patient has normal status. If one or more of the thresholds are transgressed, then method 280 proceeds to step 290 and a recommendation is determined or retrieved. Step 290 may provide a specific recommended treatment or therapy, or simply a notification of the prediction or detection, or a combination. In an embodiment, step 290 comprises determining a type of signal(s) to emit to the patient or other caregiver(s) [ordinal indicia representing 'increased likelihood' vs. 'likelihood not increased' or other categories; numeric probability; trend display; other], and/or determining whether the signal(s) to be emitted should be accompanied by specific therapy adjustment advice. Some embodiments of step 290 further include combining a signal and therapy adjustment advice (if applicable) to create a personalized advisory message.

Additionally, and/or alternatively, some embodiments of step 290 implement the aforementioned discovery by performing an action. In such an embodiment, the action may be placing new order(s) in the patient's EMR; altering the patients care plan; reserving, for the patient, resources in the care facility needed to treat and/or manage the predicted macrophage activation disorder(s); preventing and/or interrupting discharge orders from being submitted for the patient until such time as a responsible care provider has reviewed method 209's results and disabled the automatic discharge prevention measure(s); and/or, ordering increased monitoring of the patient; ordering increased testing of the patient. In an embodiment, the specific action(s) implemented may be based on the number of determined threshold transgressions.

At step 295, the determined risk level and indicated recommendation(s) (if applicable) are communicated. Some embodiments of step 295 may communicate a message to the patient and/or other caregivers, and may further store the result of the clinical calculation and communication in an electronic health record associated with the patient. In some embodiments, the patient's laboratory and/or physiologic measurements, ordered care plan, actually carried out care plan, occurrence/nonoccurrence of a macrophage activation disorder, outcome, and/or any other relevant data may be monitored and incorporated into the one or more predictive models; thereby, in an iterative processes, improving the performance of the one or more predictive models.

Further it will be understood that embodiments of method 209 may include additional and/or alternative steps; like those discussed in relation to method 200. As such, the application of embodiments of method 200 and/or 209 may result in a tangible, anticipatory change in the patient's or patients' care that prior methods and systems were incapable of achieving. Thus, by employing the techniques described herein, embodiments can overcome the deficiencies that are associated with the conventional industry practice by gathering particularized data from unique data sources and relying on unconventional techniques to overcome the tragically fatal deficiencies found within prior industry practice.

Example Reduction to Practice

With reference to FIGS. 3A-5D, and continuing reference to the drawings, an example embodiment reduced to practice is now described. Reduction to practice was accomplished using a computer running the Linux operating system (operating system 129), the open-source statistical software package R (software services 126), and the R modules (packages) entropy and fractal.

For the reduction to practice, an observational study of was performed using a consented, secondary-use-rights-granted data set. Illustrative series of self-monitoring glucometer values were retrieved from a subset of 1,667 HLH patients whose de-identified, confidentiality-protected health records were stored and maintained in Cerner's Health Facts® data warehouse. The cohort selected was comprised of 124 HLH patients for whom Health Facts® contained sufficient serial laboratory and physiologic values measured over a period of not less than 3 days but not more than 180 days.

The ranges of values of the $RMSSD_3$ for 3-sample-wide time series of a measured quantity x are calculated as:

$$RMSSD_3(x) = \sqrt{\frac{1}{N-1}\left(\sum_{i=1}^{N-1}(x_{i+1} - x_i)^2\right)} \quad \text{(Eq. 1)}$$

where N=3.

FIGS. 3A-3D shows a statistical distribution of values of the root mean square of successive differences for the 3-sample-wide time series for one of the laboratory parameters used for determining predictive models for HLH, and FIGS. 4A-4D depict RMSSD distributions.

The practice of the embodiments described herein allows latitude with regard to selecting the length of the time series upon which the forecasts are to be based. In this example embodiment actually reduced to practice, it was determined that time series that are shorter than approximately 3 samples do not contain enough representation of the variability or spectral content to yield adequate predictive accuracy for the intended purpose of assisting in determining or forecasting the presence of a macrophage activation syndrome such as HLH. It was further determined that, while incremental accuracy continued to increase for time series that were longer than 10 samples, the disadvantages of the extra time series length in terms of withholding risk predictions until the accrual of time series 10 or more samples long outweighed the benefits accompanying the incremental accuracy gains.

Furthermore, the practice of some embodiments allows latitude with regard to the length of time into the future (or the number of samples to be measured at a series of future times that will constitute a sample time series appendment to the existing already-accrued time series) for which the forecasts shall pertain. In these embodiments, where that future interval is shortened, then the likelihood of excursions outside the target range may be small, and may be reasonably well-fitted by a Poisson or negative binomial distribution. If the future interval is lengthened beyond 30 days or so, then the likelihood of excursions outside the target range becomes very large, such that the prediction is constantly high and is of little utility in a clinician's decision-making In the example reduction to practice, a forecasting time horizon of 3 to 6 samples was determined to be an effective compromise between value to the patient and the mutually-competing goals of statistical sensitivity and specificity.

Choice of suitable thresholds for the predicted probabilities of macrophage activation syndromes is not only a matter of selecting the target range and determining the mathematical/statistical model for that target range from a suitably large cohort of patients of a particular type and severity. Instead, it is also and jointly a matter of selecting the decision-level based on examination of receiver operating characteristic (ROC) curves or F1 statistics or similar means for balancing true-positive against false-positive classification rates. FIGS. 5A and 5B depict max shock index (SI) distribution in HLH patients and the number of threshold transgressions as a function of the max SI index, respectively.

False-positive (Type I) errors and persistence (delayed offsetting) of positive signals beyond the period when true-positive events are likely are, as with any predictive model, undesirable. However, in the context of clinical decision support for HLH diagnosis a modest frequency of false-positives and modest persistence of positivity are not severe faults. Moderate persistence of a positive signal serves to encourage greater vigilance on the part of the clinician. Indeed, there may be a favorable psychology to occasional false-positives or short persistence of positive signals. In other words, high statistical sensitivity in the classification-prediction use-case that is the object of this invention is a virtue.

Figure 5C:
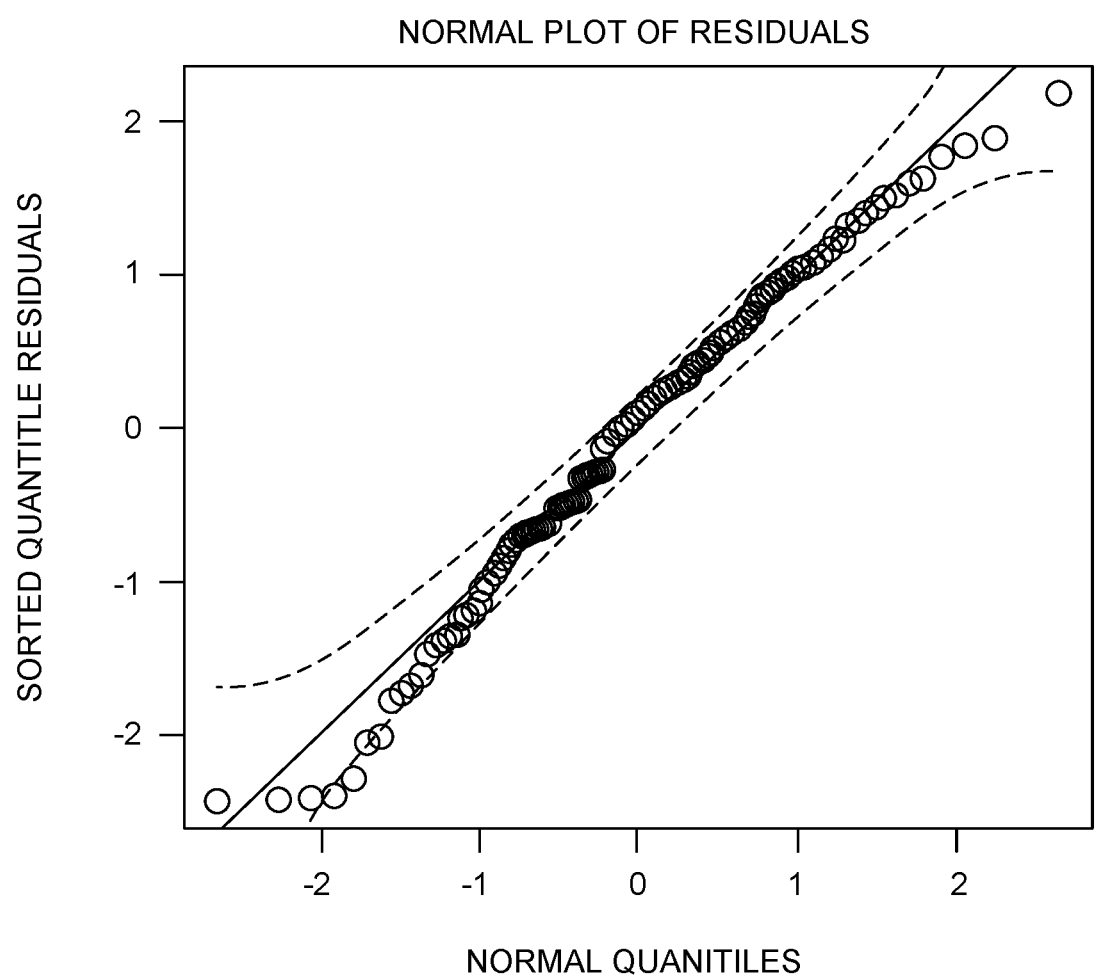
FIGS. 5C and 5D depict a Q-Q plot of copula regression and the accuracy of the predicted threshold transgressions, respectively, in accordance with an embodiment of this disclosure.
Figure 5D:
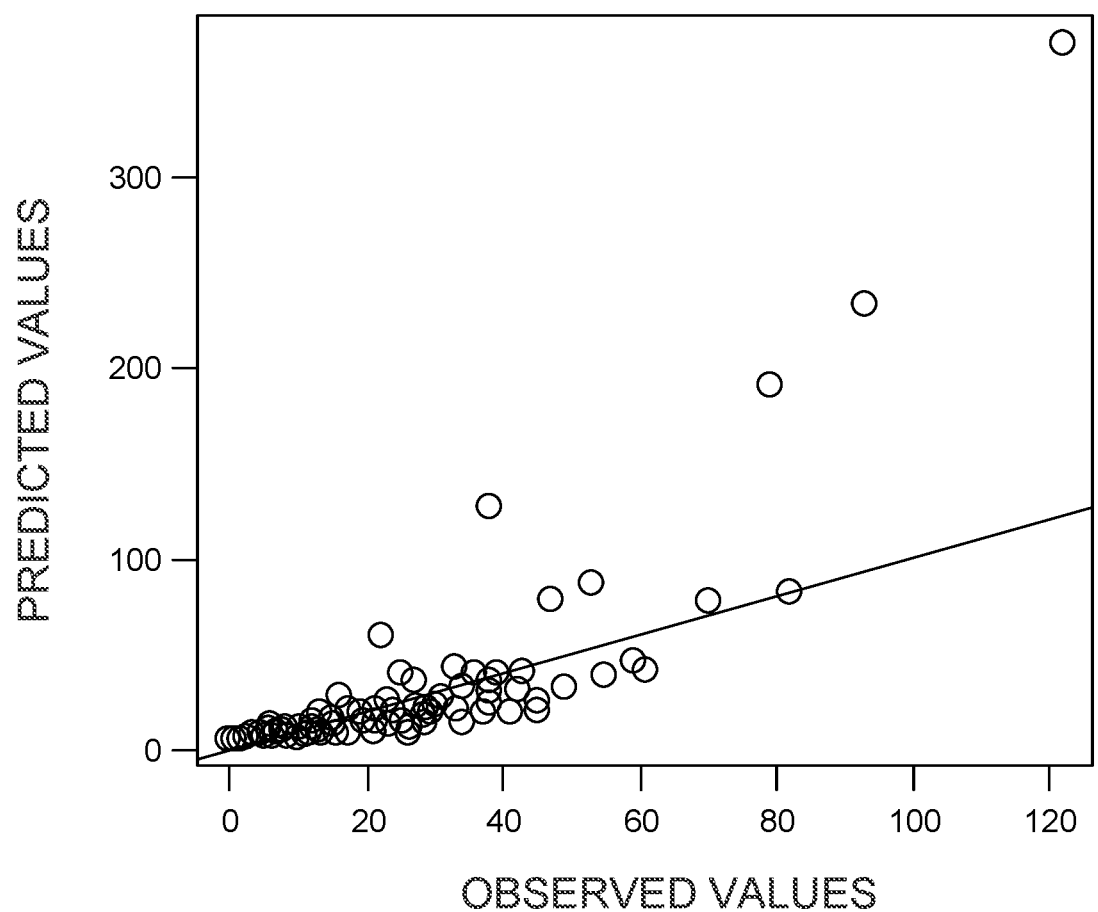

By contrast, high specificity is less important for this use-case. False-negative (Type II) errors and premature offsetting of positive signals are much to be avoided insofar as they convey false assurance of safety and may wrongly encourage the treating clinicians to be less vigilant than usual (with regard to monitoring of laboratory tests and physiologic variables, adjustment of medications, and administration of blood products or other biologics when indicated). In this way false assurances emitted by a predictive model system and method can be associated with untoward delays in diagnosing macrophage activation syndromes such as HLH. FIGS. 5C and 5D depict a Q-Q plot of copula regression and the accuracy of the predicted threshold transgressions, respectively.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A method for predicting an occurrence of a macrophage activation syndrome in a patient over a future time interval, the method comprising:
    receiving a first laboratory or physiologic measurement(s) of the patient and corresponding date-time coordinate(s);
    receiving a second laboratory or physiologic measurement(s) and a respective date-time coordinate, the second laboratory or physiologic measurement(s) being less recent than the date-time coordinate(s) corresponding to the first laboratory or physiologic measurement(s);
    receiving one or more predictive models previously determined from a population of patients in whom subsequent actual occurrences of the macrophage activation syndrome in a defined time interval were known;
    constructing a time series using at least the first laboratory or physiologic measurement(s) and the second laboratory or physiologic measurement(s), the time series constructed based on the corresponding date-time coordinate of the first laboratory or physiologic measurement(s) and the respective date-time coordinate of the second laboratory or physiologic measurement(s), the time series having at least three values associated with at least the first laboratory or physiologic measurement(s) and the second laboratory or physiologic measurement(s);
    determining a probability of the macrophage activation syndrome for the patient by calculating, for the time series having the at least three values, high-frequency components of a power spectrum or a surrogate measure of a high-frequency band of the power spectrum, the probability determined by using the one or more predictive models;
    determining the probability of the macrophage activation syndrome exceeds a threshold, the threshold associated with a condition of the patient, the first laboratory or physiologic measurement(s), the second laboratory or physiologic measurement(s), or another laboratory or physiologic measurement(s); and
    based on determining the probability of the macrophage activation syndrome exceeds the threshold, emitting a notification to a caregiver indicating that the patient has the probability, corresponding to the future time interval, of the macrophage activation syndrome exceeding the threshold.

2. The method of claim 1, wherein the surrogate measure of the high-frequency band of the power spectrum comprises a root mean square of successive deviations (RMSSD).

3. The method of claim 1, wherein the threshold is pre-determined, specific to the patient, or established for issuing an alarm to the patient or the caregiver, and wherein the threshold comprises one or more thresholds or a range.

4. The method of claim 1, wherein the future time interval is based on the one or more predictive models.

5. The method of claim 1 further comprising:
    upon emitting the notification, monitoring at least the first laboratory or physiologic measurement(s) and a diagnosis of the patient;
    determining, at least partially based on monitoring the first laboratory or physiologic measurement(s) and the diagnosis, a status of the macrophage activation syndrome;
    generating an updated one or more predictive models based on the status of the macrophage activation syndrome, the first laboratory or physiologic measurement(s), the diagnosis, and the one or more predictive models; and
    recalculating the high-frequency components of the power spectrum or the surrogate measure of the high-frequency band of the power spectrum by using the updated one or more predictive models.

6. The method of claim 1, further comprising at least one of:
    placing a new order(s) in an electronic medical record (EMR) of the patient;
    modifying a care plan of the patient;
    reserving resources, for the patient, in a care facility needed to treat the macrophage activation syndrome;
    instituting automatic discharge prevention measures, comprising preventing and interrupting discharge orders from being submitted for the patient until such time as the caregiver has reviewed the notification and disabled the automatic discharge prevention measures;
    ordering increased monitoring of the patient; and
    ordering increased testing of the patient or ordering prescriptions for the patient.

7. The method of claim 1, further comprising:
    monitoring a diagnosis of the patient;
    determining, based on the diagnosis, the occurrence or nonoccurrence of the macrophage activation syndrome; and updating, based on the occurrence of the macrophage activation syndrome, the one or more predictive models.

8. The method of claim 1, wherein the at least three values are acquired at least 24 hours apart.

9. A system for predicting an occurrence of a macrophage activation syndrome in a patient, the system comprising:
a processor; and
a computer storage medium storing computer-usable instructions that, when used by the processor, cause the processor to:
receive a first laboratory or physiologic measurement of the patient and a first associated date-time coordinate;
receive a second laboratory or physiologic measurement and a second associated date-time coordinate, the second associated date-time coordinate being less recent than the first associated date-time coordinate;
receive one or more predictive models previously determined from a population of patients in whom subsequent actual occurrences of the macrophage activation syndrome in a defined future time interval were known;
construct at least one time series using at least the first laboratory or physiologic measurement and the second laboratory or physiologic measurement, wherein the at least one time series comprises at least three values associated with the first laboratory or physiologic measurement and the second laboratory or physiologic measurement, the at least one time series constructed at least based in part on the second associated date-time coordinate being less recent than the first associated date-time coordinate;
determine a probability of the macrophage activation syndrome for the patient by calculating, for each of the at least three values, a high-frequency component of a power spectrum or a surrogate measure of a high-frequency band of the power spectrum, the probability determined by using the one or more predictive models;
determine the probability of the macrophage activation syndrome for the patient satisfies a threshold, the threshold associated with a condition of the patient, the first laboratory or physiologic measurement, the second laboratory or physiologic measurement, or another laboratory or physiologic measurement; and
based on the probability satisfying the threshold, wherein the threshold corresponds to an occurrence of the macrophage activation syndrome in the patient within a future time interval, preform an action comprising at least one of:
placing a new order in an electronic medical record (EMR) of the patient;
altering a care plan of the patient;
reserving a resource, for the patient, in a care facility for treating macrophage activation disorder(s);
modifying a plan of care for the patient that prevents, interrupts, or delays discharge orders from being submitted or carried out;
automatically scheduling increased monitoring of the patient;
ordering increased testing of the patient;
automatically scheduling a consultation with a care provider;
automatically issuing a clinical order for the patient; or
issuing an electronic alert or notification to the care provider or the patient.

10. The system of claim 9, wherein the computer storage medium stores maximum and minimum values defining target ranges for the first laboratory or physiologic measurement.

11. The system of claim 9, further comprising:
determine a plurality of future values representative of a corresponding plurality of expected levels of the patient, and
cause a display of the plurality of future values in graphical form on a computing device.

12. The system of claim 9, further comprising calculate a Hurst exponent, fractal dimension, or other self-similarity metrics of the at least one time series, and calculate an entropy or chaotic variability of the at least one time series.

13. The system of claim 9, wherein the first laboratory or physiologic measurement comprises at least one of levels of: ferritin, triglycerides, fibrinogen, erythrocytes, leukocytes, platelets, albumin, lactate dehydrogenase (LDH), creatinine, resting respiratory rate, resting heart rate, systolic blood pressure, or body temperature.

14. The system of claim 13, wherein the at least one of the levels of the LDH are from a sample of the patient, and wherein a serial serum level of the LDH is 250 U/L or greater.

15. The system of claim 13, wherein a serial serum level of the ferritin in a sample of the patient is 150 ng/mL or greater.

16. The system of claim 13, wherein a serial serum level of the fibrinogen is 200 mg/dL or less.

17. The system of claim 13, wherein a level of the triglycerides is 180 mg/dL or greater.

18. The system of claim 13 wherein:
$RMSSD_3(LDH)$ is greater than 12 U/L/day, at least one LDH level included in a calculation is greater than 250 U/L;
$RMSSD_3(ferritin)$ is greater than 15 ng/mL/day, and at least one Ferritin level included in the calculation is greater than 150 ng/mL;
$RMSSD_3(fibrinogen)$ is greater than 10 mg/dL/day, and at least one Fibrinogen level included in the calculation is less than 200 mg/dL;
$RMSSD_3(triglycerides)$ is greater than 18 mg/dL/day, and at least one Triglycerides level included in the calculation is greater than 180 mg/dL; and
wherein specimens utilized for determination of the levels and $RMSSD_3$ values are separated by not less than 24 hours and not more than 30 days.

19. One or more non-transitory computer storage media storing computer-useable instruction that, when implemented on a computing device, cause the computing device to perform operations, the operations comprising:
receiving one or more laboratory or physiologic measurements of a patient that are associated with a first set of date-time coordinates;
receiving a second one or more laboratory or physiologic measurements that are associated with a second set of date-time coordinates, the second set of date-time coordinates being less recent than the first set of date-time coordinates;
receiving one or more predictive models previously determined from a population of patients in whom subsequent actual occurrences of a macrophage activation syndrome in a defined time interval were known;
constructing at least one time series using at least the one or more laboratory or physiologic measurements and the second one or more laboratory or physiologic measurements based on the first set of date-time coordinates and the second set of date-time coordinates, wherein the at least one time series comprises at least three values associated with at least the one or more laboratory or physiologic measurements and the second one or more laboratory or physiologic measurements determining a probability of the macrophage activation syndrome for the patient by calculating, for each of the at least three values of the at least one time series, high-frequency components of a power spectrum or a surrogate measure of a high-frequency band of the power spectrum, the probability determined by using the one or more predictive models;

determining the probability of the macrophage activation syndrome for the patient satisfies one or more thresholds, the threshold associated with a condition of the patient, the one or more laboratory or physiologic measurements, the second one or more laboratory or physiologic measurement, or another laboratory or physiologic measurement; and evoking an action based on the probability satisfying the one or more thresholds, wherein the action comprises at least one of:
  causing to provide a notification to a care provider via a computing device;
  placing new order(s) in an electronic medical record (EMR) of the patient;
  altering a care plan for the patient;
  reserving resources, for the patient, in a care facility to treat the macrophage activation syndrome;
  preventing or interrupting discharge orders from being submitted for the patient until a care provider has disabled an automatic discharge prevention measure(s);
  ordering increased monitoring of the patient;
  ordering increased testing of the patient;
  ordering prescriptions for the patient; or
  issuing an electronic alert or notification to the care provider.

20. The media of claim 19, wherein the probability satisfies the one or more thresholds when the probability equals or exceeds the one or more thresholds.

* * * * *